US006413517B1

(12) United States Patent
Sette et al.

(10) Patent No.: US 6,413,517 B1
(45) Date of Patent: Jul. 2, 2002

(54) IDENTIFICATION OF BROADLY REACTIVE DR RESTRICTED EPITOPES

(75) Inventors: Alessandro Sette, La Jolla; John Sidney, San Diego; Scott Southwood, Santee, all of CA (US)

(73) Assignee: Epimmune, Inc., San Diego, CA (US)

( * ) Notice: Subject to any disclaimer, the term of this patent is extended or adjusted under 35 U.S.C. 154(b) by 0 days.

(21) Appl. No.: 09/009,953

(22) Filed: Jan. 21, 1998

Related U.S. Application Data

(60) Provisional application No. 60/036,713, filed on Jan. 23, 1997, and provisional application No. 60/037,432, filed on Feb. 7, 1997.

(51) Int. Cl.$^7$ .................. A61K 39/00; A61K 39/12; A61K 39/385; C12Q 1/68; C12N 3/00

(52) U.S. Cl. ................ 424/185.1; 424/184.1; 424/186.1; 424/193.1; 424/93.1; 424/93.2; 424/93.21; 435/172.3; 435/172.4; 435/235.1; 435/320.1; 435/325; 435/6; 514/2; 514/44; 514/15; 530/300; 530/332; 530/327; 530/868; 536/23.1; 536/23.4; 536/23.5; 536/23.92

(58) Field of Search ................ 424/93.1, 93.2, 424/93.21, 185.1, 184.1, 186.1, 193.1; 435/172.3, 172.4, 235.1, 320.1, 325, 6; 514/2, 44, 15; 530/868, 332, 300, 327; 536/23.1, 23.4, 23.5, 23.92

(56) References Cited

U.S. PATENT DOCUMENTS 5,736,142 A  4/1998  Sette et al.
5,880,103 A * 3/1999  Urban et al. .................. 514/44

FOREIGN PATENT DOCUMENTS

| WO | WO 92/02543 | 2/1992 |
| WO | WO 92/21033 | 11/1992 |
| WO | WO 93/20103 A2 | 10/1993 |
| WO | WO94/03205 A1 | 2/1994 |
| WO | WO 94/11738 | 5/1994 |
| WO | WO 95/07707 | 3/1995 |
| WO | WO 95/25122 A1 | 9/1995 |
| WO | WO 95/26982 A1 | 10/1995 |

OTHER PUBLICATIONS

Bowie et al. p. 1306; p. 1308, 1990.*
Rammensee et al, Immunogenetics; 41, 178–228, 1995.*
Marshall et al , Journal of Immunology 154; 5927–5933, 1995.*
Houghten et al, Vaccines 86; 21–25, 1986.*
Sinigaglia and Hammer Curr.Opin.Immunol 6; 52–56, 1994.*

J. Alexander et al., *Immunity* (1994) 1: 751–761.
R. Busch et al., *International Immunology* (1990) 2(5): 443–451.
K. Falk et al., *Immunogenetics* (1994) 39: 230–242.
A. Geluk et al., *Journal of Immunology* (1994) 152: 5742–5748.
J. Hammer et al., *J. Exp. Med.* (1994) 180: 2353–2358.
C.M. Hill et al., *Journal of Immunology* (1994) 152: 2890–2898.
T.S. Jardetzky et al., *The EMBO Journal* (1990) 9(6): 1797–1803.
J.I. Krieger et al., *Journal of Immunology* (1991) 146: 2331–2340.
K.W. Marshall et al., *Journal of Immunology* (1995) 154: 5927–5933.
D. O'Sullivan et al., *Journal of Immunology* (1990) 145: 1799–1808.
D. O'Sullivan et al., *Journal of Immunology* (1991) 146: 1240–1246.
D. O'Sullivan et al., *Journal of Immunology* (1991) 147: 2663–2669.
P. Panina–Bordignon et al., *Eur. J. Immunol.* (1989) 19: 2237–2242.
P.A. Roche and P. Cresswell, *Journal of Immunology* (1990) 144: 1849–1856.
O. Rotzschke and K. Falk, *Current Opinion in Immunology* (1994) 6: 45–51.
E.B. Schaeffer et al., *Proc. Nat'l Acad. Sci. USA* (1989) 86: 4649–4653.
A. Sette et al., *Journal of Immunology* (1991) 147: 3893–3900.
A. Sette et al., *Journal of Immunology* (1990) 145: 1809–1813.
A. Sette et al., *Journal of Immunology* (1993) 151: 3163–3170.
J. Sidney et al., *Journal of Immunology* (1992) 149: 2634–2640.

* cited by examiner

Primary Examiner—Jeffrey Stucker
Assistant Examiner—Padma Baskar
(74) Attorney, Agent, or Firm—Morrison & Foerster LLP; Kate H. Murashige; Bruce D. Grant

(57) ABSTRACT

The present invention is based on peptide binding specificities of HLA DR4w4, DR1 and DR7. Peptides binding to these DR molecules have a motif characterized by a large aromatic or hydrophobic residue in position 1 (Y, F, W, L, I, V, M) and a small, non charged residue in position 6 (S, T, C, A, P, V, I, L, M). In addition, allele-specific secondary effects and secondary anchors are defined, and these results were utilized to derive allele specific algorithms. By the combined use of such algorithms peptides capable of degenerate DR1, 4, 7 binding were identified.

2 Claims, 3 Drawing Sheets

Figure 1

**DRB1*0401 Algorithm: Average Relative Binding Values.**

| Residue | p1 Anchor | 2 | 3 | 4 | 5 | p6 Anchor | 7 | 8 | 9 |
|---------|-----------|------|------|------|------|-----------|-------|------|------|
| C |  | 0.57 | 0.74 | 1.12 | 0.83 | 0.47 | 0.94 | 0.28 | 1.10 |
| G |  | 1.14 | 0.64 | 0.43 | 0.48 |  | 0.49 | 1.19 | 0.52 |
| S |  | 1.55 | 1.31 | 1.29 | 1.76 | 1.11 | 1.23 | 2.93 | 1.54 |
| T |  | 1.00 | 4.34 | 0.89 | 1.32 | 1.86 | 3.07 | 1.76 | 1.64 |
| P |  | 0.56 | 0.31 | 1.44 | 2.46 | 0.86 | 2.83 | 2.12 | 2.18 |
| A |  | 0.96 | 1.04 | 1.57 | 0.59 | 0.65 | 0.86 | 0.82 | 1.62 |
| L | 0.81 | 0.86 | 1.88 | 1.28 | 1.11 | 0.67 | 1.36 | 1.08 | 0.83 |
| I | 0.79 | 1.74 | 1.01 | 1.91 | 4.39 | 0.98 | 2.36 | 1.66 | 2.75 |
| V | 0.79 | 3.34 | 0.93 | 1.05 | 0.70 | 2.36 | 0.69 | 0.54 | 1.53 |
| M | 1.14 | 12.79 | 1.49 | 2.77 | 0.32 | 0.74 | 8.11 | 1.98 | 4.05 |
| F | 2.33 | 3.66 | 1.85 | 0.80 | 1.58 |  | 1.84 | 1.34 | 1.12 |
| W | 0.82 | 2.04 | 2.52 | 0.21 | 0.91 |  | 0.39 | 0.35 | 0.22 |
| Y | 1.07 | 0.74 | 1.51 | 0.39 | 1.41 |  | 0.44 | 0.61 | 0.35 |
| H |  | 0.78 | 0.15 | 1.14 | 0.93 |  | 13.77 | 1.40 | 5.15 |
| R |  | 1.09 | 0.50 | 0.69 | 0.39 |  | 0.14 | 0.41 | 1.22 |
| K |  | 1.44 | 1.25 | 0.53 | 0.40 |  | 0.62 | 0.64 | 0.55 |
| Q |  | 0.40 | 0.38 | 1.61 | 2.09 |  | 0.31 | 0.71 | 0.62 |
| N |  | 0.44 | 1.72 | 1.42 | 1.89 |  | 0.84 | 0.43 | 1.64 |
| D |  | 0.34 | 0.33 | 1.40 | 0.40 |  | 0.58 | 0.53 | 0.24 |
| E |  | 0.31 | 1.09 | 0.42 | 0.42 |  | 0.29 | 0.61 | 0.25 |

Figure 2A

DRB1*0101 Algorithm: Average Relative Binding Values.

| Residue | p1 Anchor | 2 | 3 | 4 | 5 | p6 Anchor | 7 | 8 | 9 |
|---|---|---|---|---|---|---|---|---|---|
| C |  | 0.22 | 0.15 | 0.49 | 0.06 | 0.14 | 0.31 | 0.45 | 0.35 |
| G |  | 1.29 | 3.38 | 2.13 | 1.73 | 0.74 | 0.23 | 1.58 | 0.44 |
| S |  | 0.87 | 0.48 | 0.32 | 0.58 | 1.26 | 1.03 | 1.25 | 1.03 |
| T |  | 0.57 | 2.08 | 0.30 | 1.59 | 0.63 | 1.51 | 1.73 | 2.32 |
| P |  | 0.43 | 0.88 | 5.42 | 2.57 | 2.42 | 1.78 | 1.63 | 1.52 |
| A |  | 1.93 | 3.51 | 4.14 | 1.59 | 0.85 | 1.89 | 1.25 | 4.09 |
| L | 0.97 | 1.20 | 0.64 | 3.08 | 2.32 | 0.75 | 2.02 | 3.10 | 0.83 |
| I | 1.00 | 3.84 | 1.59 | 1.10 | 1.30 | 1.16 | 3.47 | 0.67 | 1.32 |
| V | 0.74 | 2.95 | 1.08 | 0.79 | 1.97 | 2.67 | 2.89 | 0.57 | 5.89 |
| M | 2.82 | 1.07 | 2.62 | 7.66 | 0.93 |  | 7.27 | 1.01 | 4.39 |
| F | 1.51 | 2.05 | 0.49 | 0.22 | 0.40 |  | 0.91 | 0.89 | 0.79 |
| W | 0.30 | 0.63 | 0.69 | 0.56 | 0.14 |  | 0.61 | 0.35 | 0.58 |
| Y | 0.88 | 0.51 | 1.22 | 0.36 | 2.04 |  | 0.99 | 0.26 | 0.42 |
| H |  | 0.51 | 0.11 | 0.68 | 1.57 |  | 1.81 | 1.20 | 0.55 |
| R |  | 0.80 | 0.49 | 0.43 | 0.37 |  | 1.08 | 1.43 | 0.83 |
| K |  | 2.69 | 2.32 | 0.49 | 0.67 |  | 1.33 | 2.24 | 0.44 |
| Q |  | 1.38 | 1.27 | 7.07 | 1.58 |  | 1.06 | 3.65 | 1.54 |
| N |  | 0.63 | 1.41 | 1.20 | 0.75 |  | 1.16 | 0.43 | 1.15 |
| D |  | 0.85 | 0.31 | 0.20 | 0.21 |  | 0.11 | 0.08 | 0.39 |
| E |  | 0.31 | 0.47 | 0.59 | 0.57 |  | 0.16 | 0.53 | 0.27 |

DRB1*0701 Algorithm: Average Relative Binding Values.

| Residue | p1 Anchor | 2 | 3 | 4 | 5 | p6 Anchor | 7 | 8 | 9 |
|---|---|---|---|---|---|---|---|---|---|
| C |  | 0.17 | 0.58 | 0.30 | 0.26 | 0.45 | 1.38 | 0.53 | 1.04 |
| G |  | 0.45 | 0.43 | 0.25 | 0.54 |  | 0.23 | 1.30 | 0.22 |
| S |  | 1.86 | 0.66 | 1.11 | 2.39 |  | 1.95 | 1.67 | 0.89 |
| T |  | 0.72 | 6.53 | 1.88 | 1.78 |  | 1.54 | 0.94 | 1.92 |
| P |  | 0.36 | 0.37 | 2.01 | 0.46 |  | 1.06 | 0.60 | 1.78 |
| A | 0.87 | 1.43 | 2.63 | 4.78 | 0.89 | 1.14 | 0.74 | 0.89 | 0.61 |
| L | 0.77 | 1.04 | 1.08 | 1.09 | 0.83 | 0.79 | 1.88 | 1.18 | 0.97 |
| I | 0.82 | 1.99 | 0.96 | 2.17 | 2.88 | 0.49 | 1.11 | 1.52 | 5.69 |
| V | 1.45 | 2.15 | 0.47 | 0.57 | 0.92 | 1.51 | 1.36 | 0.80 | 5.49 |
| M | 1.97 | 5.75 | 2.54 | 3.74 | 0.33 | 0.89 | 9.03 | 3.01 | 3.42 |
| F | 0.93 | 1.43 | 0.68 | 0.90 | 1.07 | 1.11 | 2.50 | 2.39 | 1.90 |
| W | 0.90 | 1.32 | 4.07 | 0.81 | 0.58 | 2.25 | 0.81 | 0.95 | 0.66 |
| Y |  | 0.78 | 3.34 | 0.62 | 3.32 | 1.21 | 0.64 | 0.74 | 0.74 |
| H |  | 1.67 | 0.36 | 0.62 | 2.09 |  | 1.10 | 1.02 | 1.13 |
| R |  | 1.29 | 0.70 | 0.45 | 1.31 |  | 0.21 | 0.59 | 2.67 |
| K |  | 1.45 | 1.32 | 0.47 | 0.86 |  | 1.40 | 1.26 | 0.48 |
| Q |  | 1.70 | 0.82 | 2.09 | 1.40 |  | 1.01 | 2.68 | 0.36 |
| N |  | 1.42 | 2.35 | 0.86 | 1.68 |  | 1.62 | 0.24 | 0.88 |
| D |  | 0.61 | 0.41 | 0.27 | 0.26 |  | 0.19 | 0.44 | 0.30 |
| E |  | 0.48 | 0.59 | 1.23 | 0.74 |  | 0.45 | 0.57 | 1.16 |

Figure 2B

SEQUENCE LISTING (1) GENERAL INFORMATION:

(iii) NUMBER OF SEQUENCES: 274

(2) INFORMATION FOR SEQ ID NO: 1:

(i) SEQUENCE CHARACTERISTICS:
       (A) LENGTH: 9 amino acids
       (B) TYPE: amino acid
       (C) STRANDEDNESS: single
       (D) TOPOLOGY: linear (ii) MOLECULE TYPE: peptide (ix) FEATURE:
       (A) NAME/KEY: Modified-site
       (B) LOCATION: 1...1
       (D) OTHER INFORMATION: Xaa = Phe, Trp, Tyr, Leu, Ile,
           Val or Met (xi) SEQUENCE DESCRIPTION: SEQ ID NO: 1:

Xaa Xaa Xaa Xaa Xaa Xaa Xaa Xaa Xaa (2) INFORMATION FOR SEQ ID NO: 2:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 2:

```
Tyr Pro Lys Tyr Val Lys Gln Asn Thr Leu Lys Leu Ala Thr
1               5                   10
```

(2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

```
Val Val His Phe Phe Lys Asn Ile Val Thr Pro Arg Thr Pro Pro Tyr
1               5                   10                  15
```

(2) INFORMATION FOR SEQ ID NO: 4:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Tyr Lys Thr Ile Ala Phe Asp Glu Glu Ala Arg Arg
1               5                   10
```

(2) INFORMATION FOR SEQ ID NO: 5:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Tyr Ala Arg Phe Gln Ser Gln Thr Thr Leu Lys Gln Lys Thr
1               5                   10
```

(2) INFORMATION FOR SEQ ID NO: 6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 6:

```
Glu Ala Leu Ile His Gln Leu Lys Ile Asn Pro Tyr Val Leu Ser
1               5                   10                  15
```

(2) INFORMATION FOR SEQ ID NO: 7:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 7:

```
Gln Tyr Ile Lys Ala Asn Ala Lys Phe Ile Gly Ile Thr Glu
1               5                   10
```

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
His Asn Trp Val Asn His Ala Val Pro Leu Ala Met Lys Leu Ile
1               5                   10                  15
```

(2) INFORMATION FOR SEQ ID NO: 9:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

```
Gly Leu Ala Tyr Lys Phe Val Val Pro Gly Ala Ala Thr Pro Tyr
1               5                   10                  15
```

(2) INFORMATION FOR SEQ ID NO: 10:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

```
Lys Ser Lys Tyr Lys Leu Ala Thr Ser Val Leu Ala Gly Leu Leu
1               5                   10                  15
```

(2) INFORMATION FOR SEQ ID NO: 11:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

```
Lys Tyr Lys Leu Ala Thr Ser Val Leu Ala Gly Leu Leu Gly Asn
1               5                   10                  15
```

(2) INFORMATION FOR SEQ ID NO: 12:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Arg His Asn Trp Val Asn His Ala Val Pro Leu Ala Met Lys Leu
1               5                   10                  15
```

(2) INFORMATION FOR SEQ ID NO: 13:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Ala Tyr Lys Phe Val Val Pro Gly Ala Ala Thr Pro Tyr Ala Gly
1               5                   10                  15
```

(2) INFORMATION FOR SEQ ID NO: 14:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Val Val Phe Pro Ala Ser Phe Phe Ile Lys Leu Pro Ile Ile Leu Ala
1               5                   10                  15
```

(2) INFORMATION FOR SEQ ID NO: 15:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Leu Thr Ser Gln Phe Phe Leu Pro Ala Leu Pro Val Phe Thr Trp Leu
1               5                   10                  15
```

(2) INFORMATION FOR SEQ ID NO: 16:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Ile Pro Gln Glu Trp Lys Pro Ala Ile Thr Val Lys Val Leu Pro Ala
 1               5                  10                  15

(2) INFORMATION FOR SEQ ID NO: 17:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 17:

Gly Pro Pro Thr Ala Leu Arg Ser Phe Gly Phe Ala Phe Gly Tyr Met
 1               5                  10                  15

(2) INFORMATION FOR SEQ ID NO: 18:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 18:

Ser Ser Val Phe Asn Val Val Asn Ser Ser Ile Gly Leu Ile Met
 1               5                  10                  15

(2) INFORMATION FOR SEQ ID NO: 19:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 19:

Val Lys Asn Val Ile Gly Pro Phe Met Lys Ala Val Cys Val Glu
 1               5                  10                  15

(2) INFORMATION FOR SEQ ID NO: 20:

(i) SEQUENCE CHARACTERISTICS:
      (A) LENGTH: 16 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 20:

Leu Phe His Tyr Tyr Phe Leu Ser Glu Lys Ala Pro Gly Ser Thr Val
 1               5                  10                  15

(2) INFORMATION FOR SEQ ID NO: 21:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 21:

Met Arg Lys Leu Ala Ile Leu Ser Val Ser Ser Phe Leu Phe Val
1               5                   10                  15

(2) INFORMATION FOR SEQ ID NO: 22:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Ser Ser Ile Ile Phe Gly Ala Phe Pro Ser Leu His Ser Gly Cys Cys
1               5                   10                  15

(2) INFORMATION FOR SEQ ID NO: 23:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Leu Val Asn Leu Leu Ile Phe His Ile Asn Gly Lys Ile Ile Lys
1               5                   10                  15

(2) INFORMATION FOR SEQ ID NO: 24:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Glu Pro Gln Gly Ser Thr Tyr Ala Ala Ser Ser Ala Thr Ser Val Asp
1               5                   10                  15

(2) INFORMATION FOR SEQ ID NO: 25:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Phe Ala Thr Cys Phe Leu Ile Pro Leu Thr Ser Gln Phe Phe Leu Pro
1               5                   10                  15

(2) INFORMATION FOR SEQ ID NO: 26:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

```
Phe Asn Val Val Asn Ser Ser Ile Gly Leu Ile Met Val Leu Ser
1               5                   10                  15
```

(2) INFORMATION FOR SEQ ID NO: 27:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

```
Ala Gly Leu Leu Gly Asn Val Ser Thr Val Leu Leu Gly Gly Val
1               5                   10                  15
```

(2) INFORMATION FOR SEQ ID NO: 28:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

```
Leu Ala Gly Leu Leu Gly Asn Val Ser Thr Val Leu Leu Gly Gly
1               5                   10                  15
```

(2) INFORMATION FOR SEQ ID NO: 29:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

```
Thr His His Tyr Phe Val Asp Leu Ile Gly Gly Ala Met Leu Ser Leu
1               5                   10                  15
```

(2) INFORMATION FOR SEQ ID NO: 30:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

```
Ile Lys Leu Pro Ile Ile Leu Ala Phe Ala Thr Cys Phe Leu Ile Pro
1               5                   10                  15
```

(2) INFORMATION FOR SEQ ID NO: 31:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Val Phe Asn Val Val Asn Ser Ser Ile Gly Leu Ile Met Val Leu
1               5                   10                  15

(2) INFORMATION FOR SEQ ID NO: 32:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

Asn Leu Ser Asn Val Leu Ala Thr Ile Thr Thr Gly Val Leu Asp Ile
1               5                   10                  15

(2) INFORMATION FOR SEQ ID NO: 33:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

Lys Phe Val Val Pro Gly Ala Ala Thr Pro Tyr Ala Gly Glu Pro
1               5                   10                  15

(2) INFORMATION FOR SEQ ID NO: 34:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Leu Ala Ala Ile Ile Phe Leu Phe Gly Pro Pro Thr Ala Leu Arg Ser
1               5                   10                  15

(2) INFORMATION FOR SEQ ID NO: 35:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Gln Glu Ile Asp Pro Leu Ser Tyr Asn Tyr Ile Pro Val Asn Ser Asn
1               5                   10                  15

(2) INFORMATION FOR SEQ ID NO: 36:

(i) SEQUENCE CHARACTERISTICS:
        (A) LENGTH: 16 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 36:

Arg Val Tyr Gln Glu Pro Gln Val Ser Pro Pro Gln Arg Ala Glu Thr
1               5                   10                  15

(2) INFORMATION FOR SEQ ID NO: 37:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Asn Val Lys Tyr Leu Val Ile Val Phe Leu Ile Phe Phe Asp Leu
1               5                   10                  15

(2) INFORMATION FOR SEQ ID NO: 38:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Leu Trp Trp Ser Thr Met Tyr Leu Thr His His Tyr Phe Val Asp Leu
1               5                   10                  15

(2) INFORMATION FOR SEQ ID NO: 39:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Trp Leu Phe Pro Arg Phe Lys Phe Val Trp Val Thr Tyr Ala Ser Trp
1               5                   10                  15

(2) INFORMATION FOR SEQ ID NO: 40:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Ile Gly Pro Phe Met Lys Ala Val Cys Val Glu Val Glu Lys Thr
1               5                   10                  15

(2) INFORMATION FOR SEQ ID NO: 41:

(i) SEQUENCE CHARACTERISTICS:
        (A) LENGTH: 15 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 41:

Ile Leu Ser Val Phe Phe Leu Ala Leu Phe Phe Ile Ile Phe Asn
1               5                  10                  15

(2) INFORMATION FOR SEQ ID NO: 42:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 42:

Lys Ser Lys Tyr Lys Leu Ala Thr Ser Val Leu Ala Gly Leu Leu
1               5                  10                  15

(2) INFORMATION FOR SEQ ID NO: 43:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 43:

Lys Tyr Lys Leu Ala Thr Ser Val Leu Ala Gly Leu Leu Gly Asn
1               5                  10                  15

(2) INFORMATION FOR SEQ ID NO: 44:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 44:

Leu Gly Asn Val Lys Tyr Leu Val Ile Val Phe Leu Ile Phe Phe
1               5                  10                  15

(2) INFORMATION FOR SEQ ID NO: 45:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 45:

Leu Ser Val Phe Phe Leu Ala Leu Phe Phe Ile Ile Phe Asn Lys
1               5                  10                  15

(2) INFORMATION FOR SEQ ID NO: 46:

(i) SEQUENCE CHARACTERISTICS:
            (A) LENGTH: 15 amino acids
```

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 46:

Leu Val Asn Leu Leu Ile Phe His Ile Asn Gly Lys Ile Ile Lys
1               5                  10                 15

(2) INFORMATION FOR SEQ ID NO: 47:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Met Lys Ile Leu Ser Val Phe Phe Leu Ala Leu Phe Phe Ile Ile
1               5                  10                 15

(2) INFORMATION FOR SEQ ID NO: 48:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Met Arg Lys Leu Ala Ile Leu Ser Val Ser Ser Phe Leu Phe Val
1               5                  10                 15

(2) INFORMATION FOR SEQ ID NO: 49:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Asn Ser Ser Ile Gly Leu Ile Met Val Leu Ser Phe Leu Phe Leu
1               5                  10                 15

(2) INFORMATION FOR SEQ ID NO: 50:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Asn Val Lys Tyr Leu Val Ile Val Phe Leu Ile Phe Phe Asp Leu
1               5                  10                 15

(2) INFORMATION FOR SEQ ID NO: 51:

(i) SEQUENCE CHARACTERISTICS:
```

(A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 51:

Ser Phe Tyr Phe Ile Leu Val Asn Leu Leu Ile Phe His Ile Asn
1               5                   10                  15

(2) INFORMATION FOR SEQ ID NO: 52:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 52:

Val Phe Phe Leu Ala Leu Phe Phe Ile Ile Phe Asn Lys Glu Ser
1               5                   10                  15

(2) INFORMATION FOR SEQ ID NO: 53:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 53:

Tyr Phe Ile Leu Val Asn Leu Leu Ile Phe His Ile Asn Gly Lys
1               5                   10                  15

(2) INFORMATION FOR SEQ ID NO: 54:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 54:

Tyr Ile Ser Phe Tyr Phe Ile Leu Val Asn Leu Leu Ile Phe His
1               5                   10                  15

(2) INFORMATION FOR SEQ ID NO: 55:

(i) SEQUENCE CHARACTERISTICS:
          (A) LENGTH: 15 amino acids
          (B) TYPE: amino acid
          (C) STRANDEDNESS: single
          (D) TOPOLOGY: linear (ii) MOLECULE TYPE: peptide (xi) SEQUENCE DESCRIPTION: SEQ ID NO: 55:

Ala Gly Leu Leu Gly Asn Val Ser Thr Val Leu Leu Gly Gly Val
1               5                   10                  15

(2) INFORMATION FOR SEQ ID NO: 56:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 56:

Ala Asn Gln Leu Val Val Ile Leu Thr Asp Gly Ile Pro Asp Ser
1               5                   10                  15

(2) INFORMATION FOR SEQ ID NO: 57:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 57:

Ala Tyr Lys Phe Val Val Pro Gly Ala Ala Thr Pro Tyr Ala Gly
1               5                   10                  15

(2) INFORMATION FOR SEQ ID NO: 58:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 58:

Asp Lys Glu Leu Thr Met Ser Asn Val Lys Asn Val Ser Gln Thr
1               5                   10                  15

(2) INFORMATION FOR SEQ ID NO: 59:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 59:

Phe Asn Val Val Asn Ser Ser Ile Gly Leu Ile Met Val Leu Ser
1               5                   10                  15

(2) INFORMATION FOR SEQ ID NO: 60:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 60:

Phe Tyr Phe Ile Leu Val Asn Leu Leu Ile Phe His Ile Asn Gly
1               5                   10                  15

(2) INFORMATION FOR SEQ ID NO: 61:

(i) SEQUENCE CHARACTERISTICS:
    (A) LENGTH: 15 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 61:

Gly Leu Ala Tyr Lys Phe Val Val Pro Gly Ala Ala Thr Pro Tyr
 1               5                  10                  15

(2) INFORMATION FOR SEQ ID NO: 62:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

Gly Arg Asp Val Gln Asn Asn Ile Val Asp Glu Ile Lys Tyr Arg
 1               5                  10                  15

(2) INFORMATION FOR SEQ ID NO: 63:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

His Ile Leu Tyr Ile Ser Phe Tyr Phe Ile Leu Val Asn Leu Leu
 1               5                  10                  15

(2) INFORMATION FOR SEQ ID NO: 64:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

His Asn Trp Val Asn His Ala Val Pro Leu Ala Met Lys Leu Ile
 1               5                  10                  15

(2) INFORMATION FOR SEQ ID NO: 65:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

Ile Val Phe Leu Ile Phe Phe Asp Leu Phe Leu Val Asn Gly Arg
 1               5                  10                  15

```
(2) INFORMATION FOR SEQ ID NO: 66:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

Lys Phe Val Val Pro Gly Ala Ala Thr Pro Tyr Ala Gly Glu Pro
 1               5                  10                  15

(2) INFORMATION FOR SEQ ID NO: 67:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

Lys Ser Leu Leu Arg Asn Leu Gly Val Ser Glu Asn Ile Phe Leu
 1               5                  10                  15

(2) INFORMATION FOR SEQ ID NO: 68:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 68:

Lys Tyr Leu Val Ile Val Phe Leu Ile Phe Phe Asp Leu Phe Leu
 1               5                  10                  15

(2) INFORMATION FOR SEQ ID NO: 69:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 69:

Leu Ala Gly Leu Leu Gly Asn Val Ser Thr Val Leu Leu Gly Gly
 1               5                  10                  15

(2) INFORMATION FOR SEQ ID NO: 70:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 70:

Leu Gly Asn Val Ser Thr Val Leu Leu Gly Gly Val Gly Leu Val
 1               5                  10                  15
```

(2) INFORMATION FOR SEQ ID NO: 71:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

```
Leu Ile Phe Phe Asp Leu Phe Leu Val Asn Gly Arg Asp Val Gln
 1               5                  10                  15
```

(2) INFORMATION FOR SEQ ID NO: 72:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

```
Leu Val Val Ile Leu Thr Asp Gly Ile Pro Asp Ser Ile Gln Asp
 1               5                  10                  15
```

(2) INFORMATION FOR SEQ ID NO: 73:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

```
Gln Leu Val Val Ile Leu Thr Asp Gly Ile Pro Asp Ser Ile Gln
 1               5                  10                  15
```

(2) INFORMATION FOR SEQ ID NO: 74:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

```
Arg Gly Tyr Tyr Ile Pro His Gln Ser Ser Leu Pro Gln Asp Asn
 1               5                  10                  15
```

(2) INFORMATION FOR SEQ ID NO: 75:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

```
Arg His Asn Trp Val Asn His Ala Val Pro Leu Ala Met Lys Leu
 1               5                  10                  15
```

(2) INFORMATION FOR SEQ ID NO: 76:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 76:

```
Arg His Pro Phe Lys Ile Gly Ser Ser Asp Pro Ala Asp Asn Ala
1               5                   10                  15
```

(2) INFORMATION FOR SEQ ID NO: 77:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 77:

```
Ser Ser Val Phe Asn Val Val Asn Ser Ser Ile Gly Leu Ile Met
1               5                   10                  15
```

(2) INFORMATION FOR SEQ ID NO: 78:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 78:

```
Val Phe Asn Val Val Asn Ser Ser Ile Gly Leu Ile Met Val Leu
1               5                   10                  15
```

(2) INFORMATION FOR SEQ ID NO: 79:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 79:

```
Val Lys Asn Val Ile Gly Pro Phe Met Lys Ala Val Cys Val Glu
1               5                   10                  15
```

(2) INFORMATION FOR SEQ ID NO: 80:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

```
Val Lys Tyr Leu Val Ile Val Phe Leu Ile Phe Phe Asp Leu Phe
```

```
        1               5                  10                  15
```

(2) INFORMATION FOR SEQ ID NO: 81:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

```
Val Ser Thr Val Leu Leu Gly Gly Val Gly Leu Val Leu Tyr Asn
 1               5                  10                  15
```

(2) INFORMATION FOR SEQ ID NO: 82:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

```
Trp Glu Asn Val Lys Asn Val Ile Gly Pro Phe Met Lys Ala Val
 1               5                  10                  15
```

(2) INFORMATION FOR SEQ ID NO: 83:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

```
Tyr Lys Phe Val Val Pro Gly Ala Ala Thr Pro Tyr Ala Gly Glu
 1               5                  10                  15
```

(2) INFORMATION FOR SEQ ID NO: 84:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 84:

```
Glu Asn Arg Trp Gln Val Met Ile Val Trp Gln Val Asp Arg Met
 1               5                  10                  15
```

(2) INFORMATION FOR SEQ ID NO: 85:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

Glu Arg Tyr Leu Lys Asp Gln Gln Leu Leu Gly Ile Trp Gly Cys Ser
1               5                   10                  15

(2) INFORMATION FOR SEQ ID NO: 86:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Glu Ser Glu Leu Val Ser Gln Ile Ile Glu Gln Leu Ile Lys Lys
1               5                   10                  15

(2) INFORMATION FOR SEQ ID NO: 87:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Phe Arg Lys Tyr Thr Ala Phe Thr Ile Pro Ser Ile Asn Asn Glu
1               5                   10                  15

(2) INFORMATION FOR SEQ ID NO: 88:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

Gly Gln Met Val His Gln Ala Ile Ser Pro Arg Thr Leu Asn Ala
1               5                   10                  15

(2) INFORMATION FOR SEQ ID NO: 89:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

Ile Pro Glu Trp Glu Phe Val Asn Thr Pro Pro Leu Val Lys Leu
1               5                   10                  15

(2) INFORMATION FOR SEQ ID NO: 90:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

```
Leu Pro Pro Val Val Ala Lys Glu Ile Val Ala Ser Cys Asp Lys
1               5                   10                  15
```

(2) INFORMATION FOR SEQ ID NO: 91:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 91:

```
Asn Arg Glu Ile Leu Lys Glu Pro Val His Gly Val Tyr Tyr Asp
1               5                   10                  15
```

(2) INFORMATION FOR SEQ ID NO: 92:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

```
Pro Ala Ile Phe Gln Ser Ser Met Thr Lys Ile Leu Glu Pro Phe
1               5                   10                  15
```

(2) INFORMATION FOR SEQ ID NO: 93:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

```
Pro Pro Val Val Ala Lys Glu Ile Val Ala Ser Cys Asp Lys Cys
1               5                   10                  15
```

(2) INFORMATION FOR SEQ ID NO: 94:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

```
Gln Glu Gln Ile Gly Trp Met Thr Asn Asn Pro Pro Ile Pro Val
1               5                   10                  15
```

(2) INFORMATION FOR SEQ ID NO: 95:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

Gln Gly Gln Met Val His Gln Ala Ile Ser Pro Arg Thr Leu Asn
1               5                   10                  15

(2) INFORMATION FOR SEQ ID NO: 96:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 96:

Ser Pro Ala Ile Phe Gln Ser Ser Met Thr Lys Ile Leu Glu Pro
1               5                   10                  15

(2) INFORMATION FOR SEQ ID NO: 97:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 97:

Thr Leu Asn Phe Pro Ile Ser Pro Ile Glu Thr Val Pro Val Lys
1               5                   10                  15

(2) INFORMATION FOR SEQ ID NO: 98:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

Val Lys Asn Trp Met Thr Glu Thr Leu Leu Val Gln Asn Ala Asn
1               5                   10                  15

(2) INFORMATION FOR SEQ ID NO: 99:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 99:

Val Pro Val Trp Lys Glu Ala Thr Thr Thr Leu Phe Cys Ala Ser
1               5                   10                  15

(2) INFORMATION FOR SEQ ID NO: 100:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 100:

Trp Glu Phe Val Asn Thr Pro Pro Leu Val Lys Leu Trp Tyr Gln
1               5                   10                  15

(2) INFORMATION FOR SEQ ID NO: 101:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 101:

Trp Val Lys Val Val Glu Glu Lys Ala Phe Ser Pro Glu Val Ile
1               5                   10                  15

(2) INFORMATION FOR SEQ ID NO: 102:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 102:

Tyr Tyr Gly Val Pro Val Trp Lys Glu Ala Thr Thr Thr Leu Phe
1               5                   10                  15

(2) INFORMATION FOR SEQ ID NO: 103:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 103:

Ala Ser Asp Phe Asn Leu Pro Pro Val Val Ala Lys Glu Ile Val
1               5                   10                  15

(2) INFORMATION FOR SEQ ID NO: 104:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 104:

Ala Ser Gly Tyr Ile Glu Ala Glu Val Ile Pro Ala Glu Thr Gly
1               5                   10                  15

(2) INFORMATION FOR SEQ ID NO: 105:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 105:

Asp Phe Asn Leu Pro Pro Val Val Ala Lys Glu Ile Val Ala Ser
 1               5                  10                  15

(2) INFORMATION FOR SEQ ID NO: 106:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 106:

Glu Ala Ile Ile Arg Ile Leu Gln Gln Leu Leu Phe Ile His Phe
 1               5                  10                  15

(2) INFORMATION FOR SEQ ID NO: 107:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

Glu Lys Val Tyr Leu Ala Trp Val Pro Ala His Lys Gly Ile Gly
 1               5                  10                  15

(2) INFORMATION FOR SEQ ID NO: 108:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 108:

Glu Thr Ala Tyr Phe Leu Leu Lys Leu Ala Gly Arg Trp Pro Val
 1               5                  10                  15

(2) INFORMATION FOR SEQ ID NO: 109:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

Glu Val Gln Leu Gly Ile Pro His Pro Ala Gly Leu Lys Lys Lys
 1               5                  10                  15

(2) INFORMATION FOR SEQ ID NO: 110:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 110:

Phe Trp Glu Val Gln Leu Gly Ile Pro His Pro Ala Gly Leu Lys
 1               5                  10                  15

(2) INFORMATION FOR SEQ ID NO: 111:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

Gly Cys Thr Leu Asn Phe Pro Ile Ser Pro Ile Glu Thr Val Pro
 1               5                  10                  15

(2) INFORMATION FOR SEQ ID NO: 112:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 112:

Gly Glu Ile Tyr Lys Arg Trp Ile Ile Leu Gly Leu Asn Lys Ile
 1               5                  10                  15

(2) INFORMATION FOR SEQ ID NO: 113:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

Gly Thr Val Leu Val Gly Pro Thr Pro Val Asn Ile Ile Gly Arg
 1               5                  10                  15

(2) INFORMATION FOR SEQ ID NO: 114:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 114:

His Lys Ala Ile Gly Thr Val Leu Val Gly Pro Thr Pro Val Asn
 1               5                  10                  15

(2) INFORMATION FOR SEQ ID NO: 115:

(i) SEQUENCE CHARACTERISTICS:
        (A) LENGTH: 15 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 115:

Ile Gly Thr Val Leu Val Gly Pro Thr Pro Val Asn Ile Ile Gly
1               5                   10                  15

(2) INFORMATION FOR SEQ ID NO: 116:

(i) SEQUENCE CHARACTERISTICS:
                (A) LENGTH: 15 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 116:

Lys Arg Trp Ile Ile Leu Gly Leu Asn Lys Ile Val Arg Met Tyr
1               5                   10                  15

(2) INFORMATION FOR SEQ ID NO: 117:

(i) SEQUENCE CHARACTERISTICS:
                (A) LENGTH: 15 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 117:

Lys Val Tyr Leu Ala Trp Val Pro Ala His Lys Gly Ile Gly Gly
1               5                   10                  15

(2) INFORMATION FOR SEQ ID NO: 118:

(i) SEQUENCE CHARACTERISTICS:
                (A) LENGTH: 16 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 118:

Leu Ile Cys Thr Thr Ala Val Pro Trp Asn Ala Ser Trp Ser Asn Lys
1               5                   10                  15

(2) INFORMATION FOR SEQ ID NO: 119:

(i) SEQUENCE CHARACTERISTICS:
                (A) LENGTH: 15 amino acids
                (B) TYPE: amino acid
                (C) STRANDEDNESS: single
                (D) TOPOLOGY: linear (ii) MOLECULE TYPE: peptide (xi) SEQUENCE DESCRIPTION: SEQ ID NO: 119:

Leu Leu Gln Leu Thr Val Trp Gly Ile Lys Gln Leu Gln Ala Arg
1               5                   10                  15

(2) INFORMATION FOR SEQ ID NO: 120:

(i) SEQUENCE CHARACTERISTICS:
                (A) LENGTH: 15 amino acids
                (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 120:

Asn Phe Pro Ile Ser Pro Ile Glu Thr Val Pro Val Lys Leu Lys
 1               5                  10                  15

(2) INFORMATION FOR SEQ ID NO: 121:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 121:

Pro Gln Gly Trp Lys Gly Ser Pro Ala Ile Phe Gln Ser Ser Met
 1               5                  10                  15

(2) INFORMATION FOR SEQ ID NO: 122:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 122:

Pro Val Asn Ile Ile Gly Arg Asn Leu Leu Thr Gln Ile Gly Cys
 1               5                  10                  15

(2) INFORMATION FOR SEQ ID NO: 123:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 123:

Gln His Leu Leu Gln Leu Thr Val Trp Gly Ile Lys Gln Leu Gln
 1               5                  10                  15

(2) INFORMATION FOR SEQ ID NO: 124:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 124:

Gln Gln His Leu Leu Gln Leu Thr Val Trp Gly Ile Lys Gln Leu
 1               5                  10                  15

(2) INFORMATION FOR SEQ ID NO: 125:

(i) SEQUENCE CHARACTERISTICS:
            (A) LENGTH: 15 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 125:

Ser Pro Glu Val Ile Pro Met Phe Ser Ala Leu Ser Glu Gly Ala
1               5                  10                  15

(2) INFORMATION FOR SEQ ID NO: 126:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 126:

Thr Lys Glu Leu Gln Lys Gln Ile Thr Lys Ile Gln Asn Phe Arg
1               5                  10                  15

(2) INFORMATION FOR SEQ ID NO: 127:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 127:

Thr Val Leu Val Gly Pro Thr Pro Val Asn Ile Ile Gly Arg Asn
1               5                  10                  15

(2) INFORMATION FOR SEQ ID NO: 128:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 128:

Val Glu Ala Ile Ile Arg Ile Leu Gln Gln Leu Leu Phe Ile His
1               5                  10                  15

(2) INFORMATION FOR SEQ ID NO: 129:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 129:

Val Ile Pro Met Phe Ser Ala Leu Ser Glu Gly Ala Thr Pro Gln
1               5                  10                  15

(2) INFORMATION FOR SEQ ID NO: 130:

(i) SEQUENCE CHARACTERISTICS:

(A) LENGTH: 15 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 130:

Val Asn Ile Ile Gly Arg Asn Leu Leu Thr Gln Ile Gly Cys Thr
1               5                   10                  15

(2) INFORMATION FOR SEQ ID NO: 131:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 131:

Trp Gly Cys Ser Gly Lys Leu Ile Cys Thr Thr Ala Val Pro Trp Asn
1               5                   10                  15

(2) INFORMATION FOR SEQ ID NO: 132:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 132:

Trp Ile Ile Leu Gly Leu Asn Lys Ile Val Arg Met Tyr Ser Pro
1               5                   10                  15

(2) INFORMATION FOR SEQ ID NO: 133:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 133:

Tyr Lys Arg Trp Ile Ile Leu Gly Leu Asn Lys Ile Val Arg Met
1               5                   10                  15

(2) INFORMATION FOR SEQ ID NO: 134:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 134:

Phe Ile Leu Val Asn Leu Leu Ile Phe His Ile Asn Gly Lys Ile
1               5                   10                  15

(2) INFORMATION FOR SEQ ID NO: 135:

```
    (i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 135:

Ala Glu Asp Leu Asn Leu Gly Asn Leu Asn Val Ser Ile Pro Trp
1               5                   10                  15

(2) INFORMATION FOR SEQ ID NO: 136:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 136:

Asp Leu Asn Leu Gly Asn Leu Asn Val Ser Ile Pro Trp Thr His
1               5                   10                  15

(2) INFORMATION FOR SEQ ID NO: 137:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 137:

Gly Phe Phe Leu Leu Thr Arg Ile Leu Thr Ile Pro Gln Ser Leu
1               5                   10                  15

(2) INFORMATION FOR SEQ ID NO: 138:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 138:

Ile Phe Leu Phe Ile Leu Leu Leu Cys Leu Ile Phe Leu Leu Val
1               5                   10                  15

(2) INFORMATION FOR SEQ ID NO: 139:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 139:

Asn Leu Asn Val Ser Ile Pro Trp Thr His Lys Val Gly Asn Phe
1               5                   10                  15

(2) INFORMATION FOR SEQ ID NO: 140:
```

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 140:

Pro Phe Leu Leu Ala Gln Phe Thr Ser Ala Ile Cys Ser Val Val
1               5                   10                  15

(2) INFORMATION FOR SEQ ID NO: 141:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 141:

Arg Phe Ser Trp Leu Ser Leu Leu Val Pro Phe Val Gln Trp Phe
1               5                   10                  15

(2) INFORMATION FOR SEQ ID NO: 142:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 142:

Ser Pro Phe Leu Leu Ala Gln Phe Thr Ser Ala Ile Cys Ser Val
1               5                   10                  15

(2) INFORMATION FOR SEQ ID NO: 143:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 143:

Ser Val Arg Phe Ser Trp Leu Ser Leu Leu Val Pro Phe Val Gln
1               5                   10                  15

(2) INFORMATION FOR SEQ ID NO: 144:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 144:

Ala Phe Ser Tyr Met Asp Asp Val Val Leu Gly Ala Lys Ser Val
1               5                   10                  15

(2) INFORMATION FOR SEQ ID NO: 145:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 145:

Ala Gly Phe Phe Leu Leu Thr Arg Ile Leu Thr Ile Pro Gln Ser
 1           5                 10             15

(2) INFORMATION FOR SEQ ID NO: 146:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 146:

Phe Val Gln Trp Phe Val Gly Leu Ser Pro Thr Val Trp Leu Ser
 1           5                 10             15

(2) INFORMATION FOR SEQ ID NO: 147:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 147:

Gly Ala His Leu Ser Leu Arg Gly Leu Pro Val Cys Ala Phe Ser
 1           5                 10             15

(2) INFORMATION FOR SEQ ID NO: 148:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 148:

Gly Thr Ser Phe Val Tyr Val Pro Ser Ala Leu Asn Pro Ala Asp
 1           5                 10             15

(2) INFORMATION FOR SEQ ID NO: 149:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 149:

Gly Val Trp Ile Arg Thr Pro Pro Ala Tyr Arg Pro Pro Asn Ala
 1           5                 10             15

(2) INFORMATION FOR SEQ ID NO: 150:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 150:

```
His Leu Ser Leu Arg Gly Leu Pro Val Cys Ala Phe Ser Ser Ala
 1               5                  10                  15
```

(2) INFORMATION FOR SEQ ID NO: 151:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 151:

```
Ile Ile Phe Leu Phe Ile Leu Leu Cys Leu Ile Phe Leu Leu
 1               5                  10                  15
```

(2) INFORMATION FOR SEQ ID NO: 152:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 152:

```
Ile Leu Leu Leu Cys Leu Ile Phe Leu Leu Val Leu Leu Asp Tyr
 1               5                  10                  15
```

(2) INFORMATION FOR SEQ ID NO: 153:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 153:

```
Ile Val Gly Leu Leu Gly Phe Ala Ala Pro Phe Thr Gln Cys Gly
 1               5                  10                  15
```

(2) INFORMATION FOR SEQ ID NO: 154:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 154:

```
Lys Phe Ala Val Pro Asn Leu Gln Ser Leu Thr Asn Leu Leu Ser
 1               5                  10                  15
```

(2) INFORMATION FOR SEQ ID NO: 155:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 155:

Leu Ala Gln Phe Thr Ser Ala Ile Cys Ser Val Val Arg Arg Ala
1               5                  10                  15

(2) INFORMATION FOR SEQ ID NO: 156:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 156:

Leu Cys Leu Ile Phe Leu Leu Val Leu Leu Asp Tyr Gln Gly Met
1               5                  10                  15

(2) INFORMATION FOR SEQ ID NO: 157:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 157:

Leu Cys Gln Val Phe Ala Asp Ala Thr Pro Thr Gly Trp Gly Leu
1               5                  10                  15

(2) INFORMATION FOR SEQ ID NO: 158:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 158:

Leu His Leu Tyr Ser His Pro Ile Ile Leu Gly Phe Arg Lys Ile
1               5                  10                  15

(2) INFORMATION FOR SEQ ID NO: 159:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 159:

Leu Leu Cys Leu Ile Phe Leu Leu Val Leu Leu Asp Tyr Gln Gly

```
                 1               5                  10                 15

(2) INFORMATION FOR SEQ ID NO: 160:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 160:

Leu Val Leu Leu Asp Tyr Gln Gly Met Leu Pro Val Cys Pro Leu
 1               5                  10                 15

(2) INFORMATION FOR SEQ ID NO: 161:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 161:

Leu Val Pro Phe Val Gln Trp Phe Val Gly Leu Ser Pro Thr Val
 1               5                  10                 15

(2) INFORMATION FOR SEQ ID NO: 162:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 162:

Pro Leu Pro Ile His Thr Ala Glu Leu Leu Ala Ala Cys Phe Ala
 1               5                  10                 15

(2) INFORMATION FOR SEQ ID NO: 163:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 163:

Gln Cys Gly Tyr Pro Ala Leu Met Pro Leu Tyr Ala Cys Ile Gln
 1               5                  10                 15

(2) INFORMATION FOR SEQ ID NO: 164:

(i) SEQUENCE CHARACTERISTICS:
         (A) LENGTH: 15 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 164:
```

```
Arg Asp Leu Leu Asp Thr Ala Ser Ala Leu Tyr Arg Glu Ala Leu
1               5                   10                  15
```

(2) INFORMATION FOR SEQ ID NO: 165:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 165:

```
Ser Phe Gly Val Trp Ile Arg Thr Pro Pro Ala Tyr Arg Pro Pro
1               5                   10                  15
```

(2) INFORMATION FOR SEQ ID NO: 166:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 166:

```
Ser Val Val Leu Ser Arg Lys Tyr Thr Ser Phe Pro Trp Leu Leu
1               5                   10                  15
```

(2) INFORMATION FOR SEQ ID NO: 167:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 167:

```
Val Gly Leu Leu Gly Phe Ala Ala Pro Phe Thr Gln Cys Gly Tyr
1               5                   10                  15
```

(2) INFORMATION FOR SEQ ID NO: 168:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 168:

```
Val Pro Asn Leu Gln Ser Leu Thr Asn Leu Leu Ser Ser Asn Leu
1               5                   10                  15
```

(2) INFORMATION FOR SEQ ID NO: 169:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 169:

```
Trp Pro Lys Phe Ala Val Pro Asn Leu Gln Ser Leu Thr Asn Leu
1               5                   10                  15
```

(2) INFORMATION FOR SEQ ID NO: 170:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 170:

```
Lys Val Leu Val Leu Asn Pro Ser Val Ala Ala Thr Leu Gly Phe
1               5                   10                  15
```

(2) INFORMATION FOR SEQ ID NO: 171:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 171:

```
Pro Thr Leu Trp Ala Arg Met Ile Leu Met Thr His Phe Phe Ser
1               5                   10                  15
```

(2) INFORMATION FOR SEQ ID NO: 172:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 172:

```
Ala Asp Leu Met Gly Tyr Ile Pro Leu Val Gly Ala Pro Leu Gly
1               5                   10                  15
```

(2) INFORMATION FOR SEQ ID NO: 173:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 173:

```
Ala Val Gln Trp Met Asn Arg Leu Ile Ala Phe Ala Ser Arg Gly
1               5                   10                  15
```

(2) INFORMATION FOR SEQ ID NO: 174:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 174:

Asp Leu Glu Leu Ile Thr Ser Cys Ser Ser Asn Val Ser Val Ala
1               5                   10                  15

(2) INFORMATION FOR SEQ ID NO: 175:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 175:

Asp Leu Tyr Leu Val Thr Arg His Ala Asp Val Ile Pro Val Arg
1               5                   10                  15

(2) INFORMATION FOR SEQ ID NO: 176:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 176:

Glu Asp Leu Val Asn Leu Leu Pro Ala Ile Leu Ser Pro Gly Ala
1               5                   10                  15

(2) INFORMATION FOR SEQ ID NO: 177:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 177:

Phe Thr Thr Leu Pro Ala Leu Ser Thr Gly Leu Ile His Leu His
1               5                   10                  15

(2) INFORMATION FOR SEQ ID NO: 178:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 178:

Gly Ala Arg Leu Val Val Leu Ala Thr Ala Thr Pro Pro Gly Ser
1               5                   10                  15

(2) INFORMATION FOR SEQ ID NO: 179:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 179:

Gly Ile Gln Tyr Leu Ala Gly Leu Ser Thr Leu Pro Gly Asn Pro
1               5                   10                  15

(2) INFORMATION FOR SEQ ID NO: 180:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 180:

Gly Val Asn Tyr Ala Thr Gly Asn Leu Pro Gly Cys Ser Phe Ser
1               5                   10                  15

(2) INFORMATION FOR SEQ ID NO: 181:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 181:

Ile Gln Tyr Leu Ala Gly Leu Ser Thr Leu Pro Gly Asn Pro Ala
1               5                   10                  15

(2) INFORMATION FOR SEQ ID NO: 182:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 182:

Leu His Gly Leu Ser Ala Phe Ser Leu His Ser Tyr Ser Pro Gly
1               5                   10                  15

(2) INFORMATION FOR SEQ ID NO: 183:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 183:

Val Asn Leu Leu Pro Ala Ile Leu Ser Pro Gly Ala Leu Val Val
1               5                   10                  15

(2) INFORMATION FOR SEQ ID NO: 184:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO: 184:

Val Gln Trp Met Asn Arg Leu Ile Ala Phe Ala Ser Arg Gly Asn
 1               5                  10                  15

(2) INFORMATION FOR SEQ ID NO: 185:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 185:

Tyr Lys Val Leu Val Leu Asn Pro Ser Val Ala Ala Thr Leu Gly
 1               5                  10                  15

(2) INFORMATION FOR SEQ ID NO: 186:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 186:

Ser Ala Leu Leu Ser Ser Asp Ile Thr Ala Ser Val Asn Cys Ala Lys
 1               5                  10                  15

(2) INFORMATION FOR SEQ ID NO: 187:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 187:

Ser Ala Leu Ser Glu Gly Ala Thr Pro Gln Asp Leu Asn Thr Met Leu
 1               5                  10                  15

(2) INFORMATION FOR SEQ ID NO: 188:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 188:

Asn Lys Ala Leu Glu Leu Phe Arg Lys Asp Ile Ala Ala Lys Tyr Lys
 1               5                  10                  15

(2) INFORMATION FOR SEQ ID NO: 189:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 189:

Asn Lys Ala Leu Glu Leu Phe Arg Lys Asp Ile Ala Ala Lys Tyr Lys
1               5                   10                  15

Glu Leu Gly Tyr
            20

(2) INFORMATION FOR SEQ ID NO: 190:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 190:

Ala Leu Glu Leu Phe Arg Lys Asp Ile Ala Ala Lys Tyr Lys Glu Leu
1               5                   10                  15

Gly Tyr (2) INFORMATION FOR SEQ ID NO: 191:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 191:

Glu Leu Phe Arg Lys Asp Ile Ala Ala Lys Tyr Lys Glu Leu Gly Tyr
1               5                   10                  15

(2) INFORMATION FOR SEQ ID NO: 192:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 192:

Met Ala Lys Thr Ile Ala Tyr Asp Glu Glu Ala Arg Arg Gly Leu Glu
1               5                   10                  15

(2) INFORMATION FOR SEQ ID NO: 193:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 193:

Lys Val Tyr Leu Pro Arg Met Lys Met Glu Glu Lys Tyr Asn Leu Thr
1               5                   10                  15

Ser Val Leu Met
            20

(2) INFORMATION FOR SEQ ID NO: 194:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 14...14
        (D) OTHER INFORMATION: Xaa = threoninamide (xi) SEQUENCE DESCRIPTION: SEQ ID NO: 194:

```
Tyr Ala Ser Phe Val Lys Thr Thr Thr Leu Arg Lys Phe Xaa
1               5                  10
```

(2) INFORMATION FOR SEQ ID NO: 195:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 195:

```
Pro His His Thr Ala Leu Arg Gln Ala Ile Leu Cys Trp Gly Glu Leu
1               5                  10                  15

Met Thr Leu Ala
            20
```

(2) INFORMATION FOR SEQ ID NO: 196:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 196:

```
Tyr Lys Met Lys Met Val His Ala Ala His Ala Lys Met Lys Met
1               5                  10                  15
```

(2) INFORMATION FOR SEQ ID NO: 197:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 197:

```
Gly Phe Tyr Thr Thr Gly Ala Val Arg Gln Ile Phe Gly Asp Tyr Lys
1               5                  10                  15

Thr Thr Ile Cys
            20
```

(2) INFORMATION FOR SEQ ID NO: 198:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 198:

Gln Asn Ile Leu Leu Ser Asn Ala Pro Leu Gly Pro Gln Phe Pro
1               5                   10                  15

(2) INFORMATION FOR SEQ ID NO: 199:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 199:

Ala Ala Tyr Ala Ala Gln Gly Tyr Lys Val Leu Val Leu Asn Pro Ser
1               5                   10                  15

Val Ala Ala Thr
            20

(2) INFORMATION FOR SEQ ID NO: 200:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 200:

Gly Tyr Lys Val Leu Val Leu Asn Pro Ser Val Ala Ala Thr Leu Gly
1               5                   10                  15

Phe Gly Ala Tyr
            20

(2) INFORMATION FOR SEQ ID NO: 201:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 201:

Gly Tyr Lys Val Leu Val Leu Asn Pro Ser Val Ala Ala Thr
1               5                   10

(2) INFORMATION FOR SEQ ID NO: 202:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 202:

```
Ser Tyr Val Asn Thr Asn Met Gly Leu Lys Phe Arg Gln Leu Leu Trp
1               5                   10                  15

Phe His Ile
```

(2) INFORMATION FOR SEQ ID NO: 203:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 203:

```
Gly Leu Lys Phe Arg Gln Leu Leu Trp Phe His Ile
1               5                   10
```

(2) INFORMATION FOR SEQ ID NO: 204:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 204:

```
Thr Leu His Gly Pro Thr Pro Leu Leu Tyr Arg Leu Gly Ala Val Gln
1               5                   10                  15

Asn Glu Ile Thr
            20
```

(2) INFORMATION FOR SEQ ID NO: 205:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 205:

```
Asn Phe Ile Ser Gly Ile Gln Tyr Leu Ala Gly Leu Ser Thr Leu Pro
1               5                   10                  15

Gly Asn Pro Ala
            20
```

(2) INFORMATION FOR SEQ ID NO: 206:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 206:

```
Gly Glu Gly Ala Val Gln Trp Met Asn Arg Leu Ile Ala Phe Ala Ser
1               5                   10                  15

Arg Gly Asn His Val
            20
```

(2) INFORMATION FOR SEQ ID NO: 207:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 207:

Lys Pro Val Ser Gln Met Arg Met Ala Thr Pro Leu Leu Met Arg Pro
1               5                   10                  15
Met (2) INFORMATION FOR SEQ ID NO: 208:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 208:

Leu Pro Lys Pro Pro Lys Pro Val Ser Lys Met Arg Met Ala Thr Pro
1               5                   10                  15
Leu Leu Met Gln Ala Leu Pro Met
            20

(2) INFORMATION FOR SEQ ID NO: 209:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 209:

Glu Tyr Leu Val Ser Phe Gly Val Trp Ile Arg Thr Pro Pro Ala
1               5                   10                  15

(2) INFORMATION FOR SEQ ID NO: 210:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 210:

Arg His Tyr Leu His Thr Leu Trp Lys Ala Gly Ile Leu Tyr Lys
1               5                   10                  15

(2) INFORMATION FOR SEQ ID NO: 211:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 211:

Trp Val Thr Val Tyr Tyr Gly Val Pro Val Trp Lys Glu Ala Thr
1               5                   10                  15

(2) INFORMATION FOR SEQ ID NO: 212:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 212:

Leu Ser Gly Ile Val Gln Gln Gln Asn Asn Leu Leu Arg Ala Ile
1               5                   10                  15

(2) INFORMATION FOR SEQ ID NO: 213:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 213:

Gly Arg Asn Leu Leu Thr Gln Ile Gly Cys Thr Leu Asn Phe Pro
1               5                   10                  15

(2) INFORMATION FOR SEQ ID NO: 214:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 214:

Gln Lys Leu Val Gly Lys Leu Asn Trp Ala Ser Gln Ile Tyr Ala
1               5                   10                  15

(2) INFORMATION FOR SEQ ID NO: 215:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 215:

Val Gly Lys Leu Asn Trp Ala Ser Gln Ile Tyr Ala Gly Ile Lys
1               5                   10                  15

(2) INFORMATION FOR SEQ ID NO: 216:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 216:

Glu Gln Leu Ile Lys Lys Glu Lys Val Tyr Leu Ala Trp Val Pro
 1               5                  10                  15

(2) INFORMATION FOR SEQ ID NO: 217:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 217:

His Ser Asn Trp Arg Ala Met Ala Ser Asp Phe Asn Leu Pro Pro
 1               5                  10                  15

(2) INFORMATION FOR SEQ ID NO: 218:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 218:

Ala Glu His Leu Lys Thr Ala Val Gln Met Ala Val Phe Ile His
 1               5                  10                  15

(2) INFORMATION FOR SEQ ID NO: 219:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 219:

Lys Thr Ala Val Gln Met Ala Val Phe Ile His Asn Phe Lys Arg
 1               5                  10                  15

(2) INFORMATION FOR SEQ ID NO: 220:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 220:

Gln Lys Gln Ile Thr Lys Ile Gln Asn Phe Arg Val Tyr Tyr Arg
 1               5                  10                  15

(2) INFORMATION FOR SEQ ID NO: 221:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 221:

```
Lys Leu Leu Trp Lys Gly Glu Gly Ala Val Val Ile Gln Asp Asn
 1               5                  10                  15
```

(2) INFORMATION FOR SEQ ID NO: 222:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 222:

```
Met Asn Tyr Tyr Gly Lys Gln Glu Asn Trp Tyr Ser Leu Lys Lys
 1               5                  10                  15
```

(2) INFORMATION FOR SEQ ID NO: 223:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 223:

```
Leu Leu Ile Phe His Ile Asn Gly Lys Ile Ile Lys Asn Ser Glu
 1               5                  10                  15
```

(2) INFORMATION FOR SEQ ID NO: 224:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 224:

```
Asn Leu Leu Ile Phe His Ile Asn Gly Lys Ile Ile Lys Asn Ser
 1               5                  10                  15
```

(2) INFORMATION FOR SEQ ID NO: 225:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 225:

```
Gln Thr Asn Phe Lys Ser Leu Leu Arg Asn Leu Gly Val Ser Glu
 1               5                  10                  15
```

(2) INFORMATION FOR SEQ ID NO: 226:

(i) SEQUENCE CHARACTERISTICS:
        (A) LENGTH: 15 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 226:

Cys Ser Val Val Arg Arg Ala Phe Pro His Cys Leu Ala Phe Ser
1               5                   10                  15

(2) INFORMATION FOR SEQ ID NO: 227:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 227:

Asn Leu Ser Trp Leu Ser Leu Asp Val Ser Ala Ala Phe Tyr His
1               5                   10                  15

(2) INFORMATION FOR SEQ ID NO: 228:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 228:

Ser Ser Asn Leu Ser Trp Leu Ser Leu Asp Val Ser Ala Ala Phe
1               5                   10                  15

(2) INFORMATION FOR SEQ ID NO: 229:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 229:

Lys Tyr Lys Ile Ala Gly Gly Ile Ala Gly Gly Leu Ala Leu Leu
1               5                   10                  15

(2) INFORMATION FOR SEQ ID NO: 230:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 230:

Ile Lys Gln Phe Ile Asn Met Trp Gln Glu Val Gly Lys Ala Met Tyr
1               5                   10                  15

(2) INFORMATION FOR SEQ ID NO: 231:

(i) SEQUENCE CHARACTERISTICS:
        (A) LENGTH: 15 amino acids
        (B) TYPE: amino acid

```
            (C) STRANDEDNESS: single
            (D) TOPOLOGY: linear (ii) MOLECULE TYPE: peptide (xi) SEQUENCE DESCRIPTION: SEQ ID NO: 231:

Leu Gln Ser Leu Thr Asn Leu Leu Ser Ser Asn Leu Ser Trp Leu
 1               5                  10                  15

(2) INFORMATION FOR SEQ ID NO: 232:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 232:

Val Gly Pro Leu Thr Val Asn Glu Lys Arg Arg Leu Lys Leu Ile
 1               5                  10                  15

(2) INFORMATION FOR SEQ ID NO: 233:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 233:

Glu Ser Arg Leu Val Val Asp Phe Ser Gln Phe Ser Arg Gly Asn
 1               5                  10                  15

(2) INFORMATION FOR SEQ ID NO: 234:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 234:

Val Val Val Val Ala Thr Asp Ala Leu Met Thr Gly Tyr Thr Gly
 1               5                  10                  15

(2) INFORMATION FOR SEQ ID NO: 235:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 235:

Thr Val Asp Phe Ser Leu Asp Pro Thr Phe Thr Ile Glu Thr Thr
 1               5                  10                  15

(2) INFORMATION FOR SEQ ID NO: 236:

(i) SEQUENCE CHARACTERISTICS:
            (A) LENGTH: 15 amino acids
```

(B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 236:

Ala Glu Thr Phe Tyr Val Asp Gly Ala Ala Asn Arg Glu Thr Lys
 1               5                  10                  15

(2) INFORMATION FOR SEQ ID NO: 237:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 237:

Glu Val Asn Ile Val Thr Asp Ser Gln Tyr Ala Leu Gly Ile Ile
 1               5                  10                  15

(2) INFORMATION FOR SEQ ID NO: 238:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 238:

Trp Ala Gly Ile Lys Gln Glu Phe Gly Ile Pro Tyr Asn Pro Gln
 1               5                  10                  15

(2) INFORMATION FOR SEQ ID NO: 239:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 239:

Gly Ala Val Val Ile Gln Asp Asn Ser Asp Ile Lys Val Val Pro
 1               5                  10                  15

(2) INFORMATION FOR SEQ ID NO: 240:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 240:

Tyr Arg Lys Ile Leu Arg Gln Arg Lys Ile Asp Arg Leu Ile Asp
 1               5                  10                  15

(2) INFORMATION FOR SEQ ID NO: 241:

(i) SEQUENCE CHARACTERISTICS:

(A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 241:

Pro Asp Ser Ile Gln Asp Ser Leu Lys Glu Ser Arg Lys Leu Asn
 1               5                  10                  15

(2) INFORMATION FOR SEQ ID NO: 242:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 242:

Lys Cys Asn Leu Tyr Ala Asp Ser Ala Trp Glu Asn Val Lys Asn
 1               5                  10                  15

(2) INFORMATION FOR SEQ ID NO: 243:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 243:

Val Tyr Leu Leu Pro Arg Arg Gly Pro Arg Leu Gly Val Arg Ala
 1               5                  10                  15

(2) INFORMATION FOR SEQ ID NO: 244:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 244:

Gly His Arg Met Ala Trp Asp Met Met Asn Trp Ser Pro Thr
 1               5                  10                  15

(2) INFORMATION FOR SEQ ID NO: 245:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 245:

Cys Gly Pro Val Tyr Cys Phe Thr Pro Ser Pro Val Val Val Gly
 1               5                  10                  15

(2) INFORMATION FOR SEQ ID NO: 246:

```
    (i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 246:

Val Tyr Cys Phe Thr Pro Ser Pro Val Val Gly Thr Thr Asp
1               5                   10                  15

(2) INFORMATION FOR SEQ ID NO: 247:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 247:

Gly Asn Trp Phe Gly Cys Thr Trp Met Asn Ser Thr Gly Phe Thr
1               5                   10                  15

(2) INFORMATION FOR SEQ ID NO: 248:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 248:

Ser Lys Gly Trp Arg Leu Leu Ala Pro Ile Thr Ala Tyr Ala Gln
1               5                   10                  15

(2) INFORMATION FOR SEQ ID NO: 249:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 249:

Ala Gln Gly Tyr Lys Val Leu Val Leu Asn Pro Ser Val Ala Ala
1               5                   10                  15

(2) INFORMATION FOR SEQ ID NO: 250:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 250:

Gly Tyr Lys Val Leu Val Leu Asn Pro Ser Val Ala Ala Thr Leu
1               5                   10                  15

(2) INFORMATION FOR SEQ ID NO: 251:
```

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 251:

Val Leu Val Leu Asn Pro Ser Val Ala Ala Thr Leu Gly Phe Gly
 1               5                  10                  15

(2) INFORMATION FOR SEQ ID NO: 252:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 252:

Asp Val Val Val Val Ala Thr Asp Ala Leu Met Thr Gly Tyr Thr
 1               5                  10                  15

(2) INFORMATION FOR SEQ ID NO: 253:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 253:

Phe Thr Gly Leu Thr His Ile Asp Ala His Phe Leu Ser Gln Thr
 1               5                  10                  15

(2) INFORMATION FOR SEQ ID NO: 254:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 254:

Tyr Leu Val Ala Tyr Gln Ala Thr Val Cys Ala Arg Ala Gln Ala
 1               5                  10                  15

(2) INFORMATION FOR SEQ ID NO: 255:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 255:

Leu Glu Val Val Thr Ser Thr Trp Val Leu Val Gly Gly Val Leu
 1               5                  10                  15

(2) INFORMATION FOR SEQ ID NO: 256:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 256:

Thr Trp Val Leu Val Gly Gly Val Leu Ala Ala Leu Ala Ala Tyr
 1               5                  10                  15

(2) INFORMATION FOR SEQ ID NO: 257:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 257:

Ala Lys His Met Trp Asn Phe Ile Ser Gly Ile Gln Tyr Leu Ala
 1               5                  10                  15

(2) INFORMATION FOR SEQ ID NO: 258:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 258:

Met Asn Arg Leu Ile Ala Phe Ala Ser Arg Gly Asn His Val Ser
 1               5                  10                  15

(2) INFORMATION FOR SEQ ID NO: 259:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 259:

Ser Tyr Thr Trp Thr Gly Ala Leu Ile Thr Pro Cys Ala Ala Glu
 1               5                  10                  15

(2) INFORMATION FOR SEQ ID NO: 260:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 260:

Gly Ser Ser Tyr Gly Phe Gln Tyr Ser Pro Gly Gln Arg Val Glu
 1               5                  10                  15

(2) INFORMATION FOR SEQ ID NO: 261:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 261:

```
Leu Glu Leu Ile Thr Ser Cys Ser Ser Asn Val Ser Val Ala His
 1               5                  10                  15
```

(2) INFORMATION FOR SEQ ID NO: 262:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 262:

```
Ala Ser Cys Leu Arg Lys Leu Gly Val Pro Pro Leu Arg Val Trp
 1               5                  10                  15
```

(2) INFORMATION FOR SEQ ID NO: 263:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 263:

```
Val Gly Asn Phe Thr Gly Leu Tyr Ser Ser Thr Val Pro Val Phe
 1               5                  10                  15
```

(2) INFORMATION FOR SEQ ID NO: 264:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 264:

```
Thr Asn Phe Leu Leu Ser Leu Gly Ile His Leu Asn Pro Asn Lys
 1               5                  10                  15
```

(2) INFORMATION FOR SEQ ID NO: 265:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 265:

```
Lys Gln Cys Phe Arg Lys Leu Pro Val Asn Arg Pro Ile Asp Trp
 1               5                  10                  15
```

(2) INFORMATION FOR SEQ ID NO: 266:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 266:

Lys Gln Ala Phe Thr Phe Ser Pro Thr Tyr Lys Ala Phe Leu Cys
1               5                   10                  15

(2) INFORMATION FOR SEQ ID NO: 267:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 267:

Ala Ala Asn Trp Ile Leu Arg Gly Thr Ser Phe Val Tyr Val Pro
1               5                   10                  15

(2) INFORMATION FOR SEQ ID NO: 268:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 268:

Pro Asp Arg Val His Phe Ala Ser Pro Leu His Val Ala Trp Arg
1               5                   10                  15

(2) INFORMATION FOR SEQ ID NO: 269:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 269:

Ile Arg Pro Val Val Ser Thr Gln Leu Leu Leu Asn Gly Ser Leu
1               5                   10                  15

(2) INFORMATION FOR SEQ ID NO: 270:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 270:

Arg Ser Glu Leu Tyr Lys Tyr Lys Val Val Lys Ile Glu Pro Leu

```
                 -continued
1          5          10         15

(2) INFORMATION FOR SEQ ID NO: 271:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 271:

Asp Arg Phe Tyr Lys Thr Leu Arg Ala Glu Gln Ala Ser Gln Glu
1               5                   10                  15

(2) INFORMATION FOR SEQ ID NO: 272:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 272:

Lys Val Ile Leu Val Ala Val His Val Ala Ser Gly Tyr Ile Glu
1               5                   10                  15

(2) INFORMATION FOR SEQ ID NO: 273:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 273:

Leu Val Asn Leu Leu Ile Phe His Ile Asn Gly Lys Ile Ile Lys Asn
1               5                   10                  15
Ser (2) INFORMATION FOR SEQ ID NO: 274:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 274:

Arg His Asn Trp Val Asn His Ala Val Pro Leu Ala Met Lys Leu Ile
1               5                   10                  15
```

IDENTIFICATION OF BROADLY REACTIVE DR RESTRICTED EPITOPES

CROSS-REFERENCE TO RELATED APPLICATIONS

The present application is a continuation in part of U.S. Ser. No. 60/036,713, filed Jan. 23, 1997 and Ser. No. 60/037,432 filed Feb. 7, 1997, both of which are incorporated herein by reference.

BACKGROUND OF THE INVENTION

Helper T lymphocytes (HTL) play several important functions in immunity to pathogens. Firstly, they provide help for induction of both CTL and antibody responses. By both direct contact and by secreting lymphokines such as IL2 and IL4, HTL promote and support the expansion and differentiation of T and B cell precursors into effector cells. In addition, HTL can also be effectors in their own right, an activity also mediated by direct cell contact and secretion of lymphokines, such as IFNγ and TNFα. HTL have been shown to have direct effector activity in case of tumors, as well as viral, bacterial, parasitic, and fungal infections.

HTL recognize a complex formed between Class II MHC molecules and antigenic peptides, usually between 10 and 20 residues long, and with an average size of between 13 and 16 amino acids. Peptide-Class II interactions have been analyzed in detail, both at the structural and functional level, and peptide motifs specific for various human and mouse Class II molecules have been proposed.

In the last few years, epitope based vaccines have received considerable attention as a possible mean to develop novel prophylactic vaccines and immunotherapeutic strategies. Selection of appropriate T and B cell epitopes should allow to focus the immune system toward conserved epitopes of pathogens which are characterized by high sequence variability (such as HIV, HCV and Malaria).

In addition, focusing the immune response towards selected determinants could be of value in the case of various chronic viral diseases and cancer, where T cells directed against the immunodominant epitopes might have been inactivated while T cells specific for subdominant epitopes might have escaped T cell tolerance. The use of epitope based vaccines also allows to avoid "suppressive" T cell determinants which induce $TH_2$ responses, in conditions where a $TH_1$ response is desirable, or vice versa.

Finally, epitope based vaccines also offer the opportunity to include in the vaccine construct epitopes that have been engineered to modulate their potency, either by increasing MHC binding affinity, or by alteration of its TCR contact residues, or both. Inclusion of completely synthetic non-natural or generically unrelated to the pathogen epitopes (such as TT derived "universal" epitopes), also represents a possible mean of modulating the HTL response toward a $TH_1$, or $TH_2$ phenotype.

Once appropriate epitope determinants have been defined, they can be assorted and delivered by various means, which include lipopeptides, viral delivery vectors, particles of viral or synthetic origin, naked or particle absorbed cDNA.

However, before appropriate epitopes can be defined, one major obstacle has to be overcome, namely the very high degree of polymorphism of the MHC molecules expressed in the human population. In fact, more than two hundred different types of HLA Class I and Class II molecules have already been identified. It has been demonstrated that in the case of HLA Class I molecules, peptides capable of binding several different HLA Class I molecules can be identified. Over 60% of the known HLA Class I molecules can, in fact, be grouped in four broad HLA supertypes, characterized by similar peptide binding specificities (HLA supermotifs).

In the case of Class II molecules, it is also known that peptides capable of binding multiple HLA types and of being immunogenic in the context of different HLA molecules do indeed exist. Until now, however, a general method for their identification has not been developed, probably at least in part a reflection of the fact that quantitative DR binding assays are labor intensive and that a large number of alleles [is?/needs?] to be considered.

The present invention addresses these and other needs.

SUMMARY OF THE INVENTION

The present invention is based, at least in part, on the discovery and validation of specific motifs and assay systems for various DR molecules, representative of the worldwide population. Their application to the identification of broadly degenerate HLA Class II binding peptides is also described.

Definitions

The term "peptide" is used interchangeably with "oligopeptide" in the present specification to designate a series of residues, typically L-amino acids, connected one to the other typically by peptide bonds between the alpha-amino and carbonyl groups of adjacent amino acids. The oligopeptides of the invention are less than about 50 residues in length and usually consist of between about 10 and about 30 residues, more usually between about 12 and 25, and often 15 and about 20 residues.

An "immunogenic peptide" is a peptide which comprises an allele-specific motif such that the peptide will bind an MHC molecule and induce a HTL response. Immunogenic peptides of the invention are capable of binding to an appropriate HLA molecule and inducing HTL response against the antigen from which the immunogenic peptide is derived.

A "conserved residue" is a conserved amino acid occupying a particular position in a peptide motif typically one where the MHC structure may provide a contact point with the immunogenic peptide. One to three, typically two, conserved residues within a peptide of defined length defines a motif for an immunogenic peptide. These residues are typically in close contact with the peptide binding groove, with their side chains buried in specific pockets of the groove itself.

The term "motif" refers to the pattern of residues of defined length, usually between about 8 to about 11 amino acids, which is recognized by a particular MHC allele.

The term "supermotif" refers to motifs that, when present in an immunogenic peptide, allow the peptide to bind more than one HLA antigen. The supermotif preferably is recognized by at least one HLA allele having a wide distribution in the human population, preferably recognized by at least two alleles, more preferably recognized by at least three alleles, and most preferably recognized by more than three alleles.

The phrases "isolated" or "biologically pure" refer to material which is substantially or essentially free from components which normally accompany it as found in its native state. Thus, the peptides of this invention do not contain materials normally associated with their in situ environment, e.g., MHC I molecules on antigen presenting cells. Even where a protein has been isolated to a homogenous or dominant band, there are trace contaminants in the range of 5–10% of native protein which co-purify with the desired protein. Isolated peptides of this invention do not contain such endogenous co-purified protein.

The term "residue" refers to an amino acid or amino acid mimetic incorporated in an oligopeptide by an amide bond or amide bond mimetic.

BRIEF DESCRIPTION OF THE DRAWINGS

FIG. 1 presents a map of the positive or negative effect of each of the 20 naturally occurring amino acids on DR4w4 binding capacity when occupying a particular position, relative to the main P1–P6 anchors.

FIG. 2A presents a map of the positive or negative effect of each of the 20 naturally occurring amino acids on DR1 binding capacity when occupying a particular position, relative to the main P1–P6 anchors.

FIG. 2B presents a map of the positive or negative effect of each of the 20 naturally occurring amino acids on DR7 binding capacity when occupying a particular position, relative to the main P1–P6 anchors.

DESCRIPTION OF THE PREFERRED EMBODIMENT

The present invention relates to compositions and methods for preventing, treating or diagnosing a number of pathological states such as viral, fungal, bacterial and parasitic diseases and cancers. In particular, it provides novel peptidase capable of binding selected major histocompatibility complex (MHC) class II molecules and inducing an immune response.

Peptide binding to MHC molecules is determined by the allelic type of the MHC molecule and the amino acid sequence of the peptide. MHC class I-binding peptides usually contain within their sequence two conserved ("anchor") residues that interact with corresponding binding pockets in the MHC molecule. Specific combination of anchor residues (usually referred to as "MHC motifs") required for binding by several allelic forms of human MHC (HLA, histocompatibility leukocyte antigens) are described in International Applications WO 94/03205 and WO 94/20127. Definition of specific MHC motifs allows one to predict from the amino acid sequence of an individual protein, which peptides have the potential of being immunogenic for CTL. These applications describe methods for preparation and use of immunogenic peptides in the treatment of disease.

The peptides described here can also be used as helper T peptides in combination with peptides which induce a CTL response. This is described in WO 95/07077.

The DR-binding peptides of the present invention or nucleic acids encoding them can be administered to mammals, particularly humans, for prophylactic and/or therapeutic purposes. The DR peptides can be used to enhance immune responses against other immunogens administered with the peptides. For instance, CTL/DR mixtures may be used to treat and/or prevent viral infection and cancer. Alternatively, immunogens which induce antibody responses can be used. Examples of diseases which can be treated using the immunogenic mixtures of DR peptides and other immunogens include prostate cancer, hepatitis B, hepatitis C, AIDS, renal carcinoma, cervical carcinoma, lymphoma, CMV and condyloma acuminatum.

The DR-binding peptides or nucleic acids encoding them may also be used to treat a variety of conditions involving unwanted T cell reactivity. Examples of diseases which can be treated using DR-binding peptides include autoimmune diseases (e.g., rheumatoid arthritis, multiple sclerosis, and myasthenia gravis), allograft rejection, allergies (e.g., pollen allergies), lyme disease, hepatitis, LCMV, post-streptococcal endocarditis, or glomerulonephritis, and food hypersensitivities.

In therapeutic applications, the immunogenic compositions or the DR-binding peptides or nucleic acids of the invention are administered to an individual already suffering from cancer, autoimmune disease, or infected with the virus of interest. Those in the incubation phase or the acute phase of the disease may be treated with the DR-binding peptides or immunogenic conjugates separately or in conjunction with other treatments, as appropriate.

In therapeutic applications, compositions comprising immunogenic compositions are administered to a patient in an amount sufficient to elicit an effective CTL response to the virus or tumor antigen and to cure or at least partially arrest symptoms and/or complications. Similarly, compositions comprising DR-binding peptides are administered in an amount sufficient to cure or at least partially arrest the symptoms of the disease and its complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician.

Therapeutically effective amounts of the immunogenic compositions of the present invention generally range for the initial immunization (that is for therapeutic or prophylactic administration) from about 1.0 µg to about 10,000 µg of peptide for a 70 kg patient, usually from about 100 to about 8000 µg, and preferably between about 200 and about 6000 µg. These doses are followed by boosting dosages of from about 1.0 µg to about 1000 µg of peptide pursuant to a boosting regimen over weeks to months depending upon the patient's response and condition by measuring specific CTL activity in the patient's blood.

It must be kept in mind that the compositions of the present invention may generally be employed in serious disease states, that is, life-threatening or potentially life-threatening situations. In such cases, in view of the minimization of extraneous substances and the relative nontoxic nature of the conjugates, it is possible and may be felt desirable by the treating physician to administer substantial excesses of these compositions.

For prophylactic use, administration should be given to risk groups. For example, protection against malaria, hepatitis, or AIDS may be accomplished by prophylactically administering compositions of the invention, thereby increasing immune capacity. Therapeutic administration may begin at the first sign of disease or the detection or surgical removal of tumors or shortly after diagnosis in the case of acute infection. This is followed by boosting doses until at least symptoms are substantially abated and for a period thereafter. In chronic infection, loading doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide mixtures or conjugates can also be used for the treatment of chronic infection and to stimulate the immune system to eliminate virus-infected cells in carriers. It is important to provide an amount of immuno-potentiating peptide in a formulation and mode of administration sufficient to effectively stimulate a cytotoxic T cell response. Thus, for treatment of chronic infection, a representative dose is in the range of about 1.0 μg to about 5000 μg, preferably about 5 μg to 1000 μg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The pharmaceutical compositions for therapeutic or prophylactic treatment are intended for parenteral, topical, oral or local administration. Typically, the pharmaceutical compositions are administered parenterally, e.g., intravenously, subcutaneously, intradermally, or intramuscularly. Because of the ease of administration, the vaccine compositions of the invention are particularly suitable for oral administration. Thus, the invention provides compositions for parenteral administration which comprise a solution of the peptides or conjugates dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of DR and/or CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides and conjugates of the invention may also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide or conjugate of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9, 467 (1980), U.S. Pat. Nos. 4,235,871, 4,501,728, 4,837, 028, and 5,019,369, incorporated herein by reference.

For targeting to the immune cells, a ligand to be incorporated into the liposome can include, e.g., antibodies or fragments thereof specific for cell surface determinants of the desired immune system cells. A liposome suspension containing a peptide or conjugate may be administered intravenously, locally, topically, etc. in a dose which varies according to, inter alia, the manner of administration, the conjugate being delivered, and the stage of the disease being treated.

Alternatively, DNA or RNA encoding one or more DR peptides and a polypeptide containing one or more CTL epitopes or antibody inducing epitopes may be introduced into patients to obtain an immune response to the polypeptides which the nucleic acid encodes. Wolff, et. al., *Science* 247: 1465–1468 (1990) describes the use of nucleic acids to produce expression of the genes which the nucleic acids encode. Such use is also disclosed in U.S. Pat. Nos. 5,580, 859 and 5,589,466.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more conjugates of the invention, and more preferably at a concentration of 25%–75%.

For aerosol administration, the peptides are preferably supplied in finely divided form along with a surfactant and propellant. Typical percentages of conjugates are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of an immunogenic DR peptide or a CTL\DR peptide conjugate or nucleic acid encoding them as described herein. The conjugate(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of the virus or tumor cells. Useful carriers are well known in the art, and include, e.g., thyroglobulin, albumins such as bovine serum albumin, tetanus toxoid, polyamino acids such as poly(lysine:glutamic acid), hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, CTL responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

Vaccine compositions containing the DR peptides of the invention are administered to a patient susceptible to or otherwise at risk of disease, such as viral infection or cancer to elicit an immune response against the antigen and thus enhance the patent's own immune response capabilities, for instance with CTL epitopes. Such an amount is defined to be an "immunogenically effective dose." In this use, the precise amounts again depend on the patient's state of health and weight, the mode of administration, the nature of the formulation, etc., but generally range from about 1.0 μg to about 5000 μg per 70 kilogram patient, more commonly from about 10 μg to about 500 μg per 70 kg of body weight.

In some instances it may be desirable to combine the peptide vaccines of the invention with vaccines which induce neutralizing antibody responses to the virus of interest, particularly to viral envelope antigens. For instance, PADRE peptides can be combined with hepatitis vaccines to increase potency or broaden population coverage. Suitable hepatitis vaccines that can be used in this manner include, Recombivax HB® (Merck) and Engerix-B (Smith-Kline).

For therapeutic or immunization purposes, the peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL response. Vaccinia vectors and methods useful in immunization protocols are described in, e.g., U.S. Pat. No. 4,722, 848, incorporated herein by reference. Another vector is BCG (Bacille Calmette Guerin). BCG vectors are described in Stover et al., Nature 351, 456–460 (1991)) which is incorporated herein by reference. A wide variety of other vectors useful for therapeutic administration or immunization of the peptides of the invention, e.g., *Salmonella typhi* vectors and the like, will be apparent to those skilled in the art from the description herein.

Antigenic conjugates may be used to elicit CTL ex vivo, as well. The resulting CTL can be used to treat chronic infections (viral or bacterial) or tumors in patients that do not respond to other conventional forms of therapy, or will not respond to a peptide vaccine approach of therapy. Ex vivo CTL responses to a particular pathogen (infectious agent or tumor antigen) are induced by incubating in tissue culture the patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will destroy their specific target cell (an infected cell or a tumor cell).

The peptides of this invention may also be used to make monoclonal antibodies. Such antibodies may be useful as potential diagnostic or therapeutic agents.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

EXAMPLE

Materials and Methods

Cells. The following Epstein-Barr virus (EBV) transformed homozygous cell lines were used as sources of human HLA Class II molecules: LG2 [DRB1c0101 (DR1)1; GM3107 [DRB50101 (DR2w2a)]; MAT (DRB10301 (DR3) 1; PREISS [DRB10401 (DR4w4)1; BIN40 [DRB10404 (DR4w14)1; SWEIG [DRB11101 (DR5w11)]; PITOUT [DRB10701 (DR7)] (a); KT3 [DRB10405 (DR4w15)]; Herluf [DRB11201 (DR5w12)]; H0301 [DRB11302 (DR6w19)]; OLL [DRB10802 (DR8w2)]; and HTC9074 [DRB10901 (DR9), supplied as a kind gift by Dr. Paul Harris, Columbia University]. In some instances, transfected fibroblasts were used: L466.1 [DRB11501 (DR2w2b)]; TR81.19 [DRB30101 (DR52a)]; and L257.6 [DRB40101 (DRw53)]. (Valli, et al. *J. Clin. Invest.* 91:616 (1993). Cells were maintained in vitro by culture in RPMI 1640 medium supplemented with 2 mM L-glutamine [GIBCO, Grand Island, N.Y.], 50 μM 2-ME, and 10% heat-inactivated FCS [Irvine Scientific, Santa Ana, Calif.]. Cells were also supplemented with 100 μg/ml of streptomycin and 100U/ml of penicillin [Irvine Scientific]. Large quantities of cells were grown in spinner cultures.

Cells were lysed at a concentration of $10^8$ cells/ml in PBS containing 1% NP-40 [Fluka Biochemika, Buchs, Switzerland], 1 mM PMSF [CalBioChem, La Jolla, Calif.], 5 mM Na-orthovanadate, and 25 mM iodoacetamide [Sigma Chemical, St. Louis, Mo. ]. The lysates were cleared of debris and nuclei by centrifugation at 10,000×g for 20 min. Affinity purification of HLA-DR molecules. Class II molecules were purified by affinity chromatography as previously described (Sette, et al. *J. Immunol.* 142:35 (1989) and Gorga, et al. *J. Biol. Chem.* 262:16087 (1987)) using the mAb LB3.1 coupled to Sepharose 4B beads. Lysates were filtered through 0.8 and 0.4 μM filters and then passed over the anti-DR column, which were then washed with 15-column volumes of 10 mM TRIS in 1% NP-40, PBS and 2-column volumes of PBS containing 0.4% n-octylglucoside. Finally, the DR was eluted with 50 mM diethylamine in 0. 15M NaCl containing 0.4% n-octylglucoside, pH 11.5. A 1/25 volume of 2.0M Tris, pH 6.8, was added to the eluate to reduce the pH to ~8.0, and then concentrated by centrifugation in Centriprep 30 concentrators at 2000 rpm (Amicon, Beverly, Mass.).

Class II peptide-binding assays. A panel of 13 different specific DR-peptide assays were utilized in the present study. These assays were chosen as to be representative of the most common DR alleles. Table I lists for each DR antigen, the representative allelic product utilized, the cell line utilized as a source of DR, and the radiolabeled probe utilized in the assay. Purified human Class II molecules [5 to 500 nM] were incubated with various unlabeled peptide inhibitors and 1–10 nM $^{125}$I-radiolabeled probe peptides for 48 h in PBS containing 5% DMSO in the presence of a protease inhibitor cocktail. The radiolabeled probes used were HA Y307–319 (DR1), Tetanus Toxoid[TT] 830–843 (DR2w2a, DR5w111, DR7, DR8w2, DR8w3, DR9), MBP Y85–100 (DR2w2b), TT1272–1284 (DR52a), MT 65 kD Y3–13 with Y7 substituted with F for DR3, a non-natural peptide with the sequence YARFQSQTTLKQKT (SEQ ID NO:5) (DR4w4, DR4w15, DRw53) (Valli, et al. supra), and for DR5w12, a naturally processed peptide eluted from the cell line C1R, EALIHQLINPYVLS (SEQ ID NO:6) (DR5w12) and 650.22 peptide, (TT 830–843 A→S836 analog), for DR6w19.

Radiolabeled peptides were iodinated using the chloramine-T method. Peptide inhibitors were typically tested at concentrations ranging from 1201 µg/ml to 1.2 ng/ml. The data were then plotted and the dose yielding 50% inhibition (IC50) was measured. In appropriate stoichiometric conditions, the IC50 of an unlabeled test peptide to the purified DR is a reasonable approximation of the affinity of interaction (Kd). Peptides were tested in two to four completely independent experiments. The final concentrations of protease inhibitors were: 1 mM PMSF, 1.3 nM 1.10 phenanthroline, 73 µM pepstatin A, 8 mM EDTA, and 200 µM N alpha-p-tosyl-L-lysine chloromethyl ketone (TLCK) [All protease inhibitors from CalBioChem, La Jolla, Calif.]. Final detergent concentration in the incubation mixture was 0.05% Nonidet P-40. Assays were performed at pH 7.0 with the exception of DR3, which was performed at pH 4.5, and DRw53, which was performed at pH 5.0. The pH was adjusted as previously described (Sette, et al. *J. Immunol.* 148:844 (1992)).

Class II peptide complexes were separated from free peptide by gel filtration on TSK2000 columns (TosoHaas 16215, Montgomeryville, Pa.), and the fraction of bound peptide calculated as previously described (Sette, et al., (1989) supra). In preliminary experiments, the DR prep was titered in the presence of fixed amounts of radiolabeled peptides to determine the concentration of Class II molecules necessary to bind 10–20% of the total radioactivity. All subsequent inhibition and direct binding assays were the performed using these Class II concentrations.

DRB1 Specificity of DR4w15, DR6w19, DR8w2, DR8w3, and DR9 Assays.

Because the antibody used for purification is α-chain specific, β1 molecules are not separated from β3 (and/or β4 and β5) molecules. Development and validation of assays in regard with DRβ chain specificity has been described in detail elsewhere for many of the DR alleles listed above (108). Herein we describe for the first time DR4w15, DR6w19, DR8w2, DR8w3, and DR9 assays. Experiments addressing the β chain specificity of these new assays are described in the present section.

DR4w15. The β4 product DRw53 is co-expressed with DR4w15 and the determination of the specificity of the DR4w15 binding assay is complicated in that the same radiolabeled ligand is used for both the DR4w15 and DRw53 binding assays. Since typically β1 chains are expressed at 5–10 fold higher levels than other β chains, and all binding assays are performed utilizing limiting DR amounts, it would be predicted that the dominant specificity detected in the assay would be DR4w15. To verify that this was indeed the case, the binding pattern of a panel of 58 different synthetic peptides in the putative DR4w15 specific assay with that obtained in a DRw53 specific assay (which uses a DRw53 fibroblast as the source of Class II molecules). Two very distinct binding patterns were noted, and in several instances, a peptide bound to one DR molecule with high affinity, and did not bind to the other (data not shown).

DR6w19. The DR6w19 assay utilizes as the source of Class II molecules the EBV transformed homozygous cell line H0301, which co-expresses DRB30301 (DR52a). While the radiolabeled ligand used in the DR6w19 assay is different than that used for the DR52a assay, the ligand is related (i.e., is a single substitution analog) to a high affinity DR52a binder. As was done in the case of DR4w15, the specificity of the assay was investigated by analyzing the binding capacity of a panel of naturally occurring peptides for DR6w19 and DR52a. The two assays demonstrated completely different binding specificities. For example, in terms of relative binding, TT 1272–1284 binds 63-fold better in the DR52a assay than in the DR6w19 assay. Conversely, the Invariant chain peptide binds 189-fold better in the DR6w19 assay. In conclusion, these data demonstrated that the binding of the radiolabeled peptide 650.22 to purified Class II MHC from the H0301 cell line is specific for DR6w19.

DR8w2 and DR8w3. The β1 specificity of the DR8w2 and DR8w3 assays is obvious in that no β3 (and/or β4 and β5) molecule is expressed.

DR9. The specificity of DR9 assay is inferred from previous studies which have shown that the TT 830–843 radiolabeled probe peptide does not bind to DRw53 molecules (Alexander, et al., *Immunity* 1:751 (1994)).

Results
DR Binding Affinity of Antigenic Peptides Recognized by DR Restricted T Cells To define a threshold DR binding affinity, to be considered as biologically significant, we compiled the affinities of a panel of 32 reported instances of DR restriction of a given T cell epitope. In approximately half of the cases, DR restriction was associated with affinities of less than 100 nM, and in the other half of the instances, with IC50% in the 100–1000 nM range. Only in 1 out of 32 cases (3.1%) DR restriction was associated with IC50% of 1000 nM or greater. It was noted that this distribution of affinities differs from what was previously reported for HLA class I epitopes, where a vast majority of epitopes bound with IC50% of 50 nM or less (Sette, et al., JI, 1994). This relatively lower affinity of class II restricted epitope interactions might explain why activation of class II restricted T cells in general requires more antigen relative to class I restricted T cells.

In conclusion, this analysis suggested that 1000 nM may be defined as an affinity threshold associated with immunogenicity in the context of DR molecules, and for this reason a suitable target for our studies.

P1 and P6 Anchors are Necessary but not Sufficient for DRB10401 Binding

Several independent studies have pointed to a crucial role in DRB10401 binding of a large aromatic or hydrophobic residue in position 1, near the N-terminus of the peptide and of a 9-residue core region (residues 1 through 9). In addition, an important role has been demonstrated for the residue in position six (P6) of this 9-residues core region. Short and/or hydrophobic residues were in general preferred in this position (O'Sullivan, et al., JI 147:2663, 1991; Sette, et al., JI 151:3163, 1993; Hammer, et al., Cell 74:197, 1993 and Marshall, et al., JI 154:5927, 1995).

In the present set of experiments, a library of 384 peptides was analyzed for DRB10401 binding capacity and screened for the presence of the P1–P6 motif (that is, F, W, Y, L, I, V or M in P1 and S, T, C, A, P, V, I, L or M in P6, at least 9 residues apart from the peptide C-terminus (SEQ ID NO;1). This set of 384 peptides contained a total of 80 DR4w4 binders (specifically 27 good binders [IC50 of 100 nM or less], and 53 intermediate binders [IC50 of the 100–1000 range]. Seventy-seven out of the 80 DR4w4 binders (96%)

carried the P1–P6 motif. However, it should be noted that most non-DR4w4 binding peptides also contained the P1–P6 motif. Of 384 peptides included in our database, only 125 were "P1–P6 negative." Only three of them (6%) bound appreciably to purified DR4w4 as opposed to 77/259 (30%) of the "P1-P6 positive" peptides. Therefore, these results demonstrate that presence of suitable P1 and P6 anchors are necessary but not sufficient for DRB10401 binding.

A Detailed Map of DRB10401 Peptide Interactions

Next, for each P1–P6 aligned core region, in analogy with what the strategy previously utilized to detail peptide class I interactions the average binding affinity of peptides carrying a particular residue, relative to the remainder of the group, were calculated for each position. Following this method a table of average relative binding (ARB) values was compiled. This table also represents a map of the positive or negative effect of each of the 20 naturally occurring amino acids on DRB10401 binding capacity when occupying a particular position, relative to the main P1–P6 anchors (FIG. 1).

Variations in ARB values greater than four fold (ARB≧4 or ≦0.25) were arbitrarily considered significant and indicative of secondary effects of a given residue on DR-peptide interactions. Most secondary effects were associated with positions 4, 7, and 9. These positions correspond to secondary anchors engaging shallow pockets on the DR molecule. In addition, significant secondary effects were detected for M in position 3 (ARB=12.8) T in position 3 (ARB=4.34) and I in position 5 (ARB=4.4).

Development of a DRB10401 Specific Algorithm

Next, the ARB table was utilized to develop a DRB10401 specific algorithm. In order to predict 0401 binding propensity, each aligned P1–P6 sequence was scored by multiplying, for each position, the ARB value of the appropriate amino acid. According to this procedure, a numerical "algorithm score" was derived. If multiple P1–P6 alignments were possible, binding scores were calculated for each one and the best score was selected. The efficacy of this method in predicting 0401 binding capacity is shown in Table IIa.

Considering only peptides with algorithm scores above –17.00 narrowed the set of predicted peptides to 156. This set still contained 72 out of 80 (90%) of the total high or intermediate DR binders. Raising the cut-off to an algorithm score of –16.44 or higher still allowed identification of 60 out of 80 (75%) of the DR4w4 binding peptides. Of the whole 107 peptide set, twenty-five of them were either good or intermediate binders. In other words, as expected, increasing the algorithm score stringency predicted a smaller fraction of the total binders present in the set, but at the same time less false positive peptides were identified.

Blind Test of the Predictive Power of the DRB10401 Specific Algorithm

To verify that the predictive capacity of our algorithm was not merely a reflection of having utilized the same data set to test and define the algorithm itself, we further examined its efficacy in a blind prediction test. For this scope we utilized data from an independent set of 50 peptides, whose binding affinities were known, but that had not been utilized in the derivation of the algorithm. As shown in Table IIb, the algorithm was effective in predicting DR4w4 binding capacity of this independent peptide set. The algorithm score of –17.00 identified a total 18 peptides. This set contained 3/3 (100%) of all good binders, and 8/11 (70%) of all intermediate binders in the entire test set of 50 peptides. Increasing the cut-off value to –16.44, identified a set of nine peptides. Seven of them (78%) were either good or intermediate binders. This set contained 7 out of 14 (50%) of the binders contained in the blind prediction peptide set. In conclusion, these data supports the validity of the DR4w4 specific algorithm described above.

Detailed Maps of DRB10401, DRB10101, and DRB10701 Peptide Binding Specificities

Next, we analyzed the binding to purified DR1 and DR7 molecules for the same set of 384 peptides utilized to define the DR4w4 algorithm. It was found that this set contained 120 and 59 binders for the DR1 and DR7 alleles, respectively. A total of 158 peptides were capable of binding either DR1, DR4w4 or DR7. A large fraction of them (73/158; 46%) were also degenerate binders, which bound two or more of the three alleles thus far considered. Furthermore, we also found that more than 90% of the DR1 or DR7 good and intermediate binders carried the P1–P6 motif. Most importantly, 72 out of 73 (99%) degenerate DR binders carried this motif (data not shown). In conclusion, this analysis suggests that P1–P6 based algorithms might be utilized to effectively predict degenerate DR binders.

In analogy with what was described above for DR4w4 molecules, specific algorithms were designed for the DR1 and DR7 alleles. FIGS. 2A and 2B detail the allele specific maps defined according to this method.

As in the case of DRB10401, most secondary effects were concentrated in positions 4, 7 and 9. Position 4 was especially prominent in the case of DR1, while position 7 was the most prominent secondary anchor for DR7. Specific algorithms were developed based on these maps, and it was found that the cut-off values necessary to predict 75% or 90% of the binders were –19.32 and –20.28 for DR1, and 20.91 and –21.63 for DR7, respectively. Depending on the particular allele or cut off value selected, 40 to 60% of the predicted peptides were in fact good or intermediate binders (data not shown).

Development of a DR1-4-7 Combined Algorithm

Finally, we examined whether a combined algorithm would allow to predict degenerate binders. For this purpose, the sequences of the 384 peptides in our database were simultaneously screened with the three (DR1, 4w4, and 7) specific algorithms. It was found that an even 100 peptides were predicted (using the 75% cut off) to bind either two or three of the alleles considered. This set contained 59 out of 73 (81%) of the peptides which were in fact capable of degenerate 1-4-7 binding (defined as the capacity to bind to more than one of the DR1, 4w4 or 7 alleles) (Table III).

Definition of a Target Set of DR Specificities, Representative of the World Population The data presented in the preceding sections illustrates how peptides capable of binding multiple DR alleles can be identified by the use of a combined "1-4-7"-algorithm. Next, we wished to examine whether the peptides exhibiting degenerate 1-4-7 binding behavior would also bind other common DR types as well. As a first step in our experimental strategy, we sought to define a set of target DR types representative of a large (≧80%) fraction of the world population, irrespective of the ethnic population of origin. For this purpose, seven additional DR antigens were considered. For each one of the DR antigens considered in this study, (including DR1, 4 and 7), the estimated frequency in various ethnicities, according to the most recent HLA workshop (11th, 1991) is shown in Table IVa, together with the main subtypes thus far identified.

For the purpose of measuring peptide binding affinity to the various DR molecules, one representative subtype for each DR antigen was chosen (Table I). It should be noted that for most antigens, either one subtype is by far the most abundant, or alternatively a significant degree of similarity in the binding pattern displayed by the different, most abundant subtypes of each DR antigen is likely to exist (see comments column of Table IVb). One exception to this general trend is represented by the DR4 antigen, for which significant differences in peptide specificity between the 0401 and 0405 have been reported. Since both alleles are quite frequent (in Caucasians and Orientals, respectively) we included both DR 0401 and 0405 in the set of representative DR binding assays.

Our set of representative assays is mostly focused on allelic products of the gene, because these molecules appear to be the most abundantly expressed, serve as the dominant restricting element of most human class III responses analyzed thus far, and accurate methods for serologic and DNA typing most readily available. However, we have also considered in our analysis assays representative of DRB3/4/5 molecules (Table IVc). These molecules serve as a functional restriction element, and their peptide binding specificity has been previously shown to have certain similarities to the specificity of several common $DR\beta_1$ allelic products.
A General Strategy for Prediction of DR-degenerate Binders.

To test whether the 1-4-7 combined algorithm would also predict degenerate binding to other common DR types, we measured the capacity of three different groups of synthetic peptides to bind the panel of purified HLA DR molecules. The three different peptide sets were: A) 36 peptides which did not score positive in the combined 1-4-7 algorithm (non-predictions), B) 36 peptides which did score positive for the 1–4–7 algorithm, at the 75% cut off level, but had been found upon actual testing not to be degenerate 1-4-7 binders ("wrong" predictions), and C) 29 peptides which scored positive in the 1-4-7 algorithm, and also proved upon experimental testing, to be actual 1-4-7 degenerate binders (correct predictions). The results of this analysis are shown in Table V.

Within the set of "non-predictions" peptides (Table Va) only 3 out of 34 (9%) bound at least two of the DR1, 4w4 or 7 molecules. Interestingly, 2 (1136.04 and 1136.29) out of 3 of these peptides were also rather crossreactive, and bound additional DR types (DR2w2 β2, DR4w15, 5w11 and 8w2 in the case of 1136.04, and 2w2 β2, 4w15, 9 and 5w12 in the case of 1136.29). Peptides from the "wrong predictions" peptide set (Table V5), by definition bound at the most only one of the DR1, 4w4 or DR7 molecules, and were also poorly degenerate or other DR types with only two peptides (1136.22 and 1188.35) binding a total of three DR molecules. Within this peptide set, no peptide bound four or more of the DR molecules tested (data not shown).

These results are contrasted by data obtained with the peptide set corresponding to peptides which were first predicted by the use of the combined 1, 4, 7 algorithm, and then experimentally found to be degenerate DR1-4-7 binding. Fourteen out of 29 peptides tested (48%) bound a total of five or more alleles. Four of them were remarkably degenerate (1188.16, 1188.32, 1188.34 and F107.09) and bound a total of nine out of the 11 DR molecules tested. In conclusion, these results suggest that a strategy based on the sequential use of a combined DR1, 4, 7 algorithm and quantitative DR1, 4, 7 binding assays can be utilized to identify broadly crossreactive DR binding peptides.
Definition of the HLA-DR 1-4-7 Supertype The data presented above also suggested that several common DR types are characterized by largely overlapping peptide binding repertoires. When this issue was analyzed in more detail, by analyzing the binding pattern of the thirty-two peptides from Table Va and b which were actual DR1-4-7 degenerate binders. Thirty-one of them (97%) bound DR1, 22 (69%) DR4w4 and 21 (66%) DR7. These files are contrasted with the low percentages of binding observed amongst the remainder non-degenerate binding peptides (17/67 (25%), 8/67 (12%) and 7/67 (10%), for DR1, 4w4 and 7, respectively) (Table VII).

Interestingly, a large fraction of the 1-4-7 degenerate binders also bound certain other common DR types. Sixteen (50%) bound DR2w2a, 18 (56%) DR6w19, 18 (56%) DR2w2b and 20 (62%) DR9. In all cases, the frequency of binding in the non-1-4-7 degenerate peptide set was much lower (Table VIII).

Significant, albeit lower, frequencies of cross reactivity were noted also for DR4w15, DR5w11, and DR8w2 (in the 28 to 37% range). Finally, negligible levels of cross reactivity were observed in the case of DR3 and 5w12 and DR53. Further studies will address whether either of these two group of molecules (DR4w15, 5w 1 , and 8w2 on one hand, and DR3, DR53 and 5w12 on the other) might belong to different DR supertypes.

In conclusion, these data demonstrates that a large set of DR molecules encompassing DR1, 4w4, 2w2a, 2w2b, 7, 9 and 6w19 is characterized by largely overlapping peptide binding repertoires.

Discussion

In the present report we have analyzed the peptide binding specificity of a set of 13 different DR molecules, representative of DR types common among the worldwide population. Detailed maps of secondary anchors and secondary interactions have been derived for three of them (DR4w4, DR1 and DR7). Furthermore, we demonstrated that a set of at least seven different DR types share overlapping peptide binding repertoires; and consequently that broadly degenerate HLA DR binding peptides are a relatively common occurrence. This study also describes computerized procedures which should greatly assist in the task of identification of such degenerate peptides.

We would like to discuss the data in the context of our current understanding of peptide-class II interactions, as well as in the context of the recently described class I supermotifs. Finally, the potential implications of broadly degenerate class II epitopes for epitope based vaccine design should also be considered.

Firstly, our studies illustrate how the vast majority of the peptides binding with good affinity to DR4w4, DR1, DR7 and most of the other DR types analyzed in the current study (data not shown), are all characterized by a P1–P6 motif consistent with the one originally proposed by O'Sullivan, et al. Crystallographic analysis of DR1-peptide complexes revealed that the residues occupying these positions engage two complementary pockets on the DR1 molecule, with the P1 position corresponding to the most crucial anchor residue and the deepest hydrophobic pocket. Our analysis also illustrates how other "secondary anchor" positions drastically influence in an allele-specific manner peptide binding capacity. Position 4 was found to be particularly crucial for DR1 binding, position 9 for DR4w4, and position 7 for DR7. These data are consistent with previous results which originally described such allele-specific anchors, and with crystallographic data which illustrates how these residues engage shallow pockets on the DR molecule.

Secondly, our studies illustrate how an approach based on alignment and calculation of average relative binding values of large peptide libraries allows definition of quantitative algorithms to predict binding capacity. The present study extends those observations to two other common HLA-DR types, and also illustrates how the combined use of the 1-4-7 algorithms can be of aid in identifying broadly degenerate DR binding peptides.

The data presented herein suggest that a group of common DR alleles, including at least DR1, DR2w2a, DR2w2b, DR4w4, DR6w19, DR7 and DR9 share a largely overlapping peptide repertoire. Degenerate peptide binding to multiple DR alleles, and recognition of the same epitope in the context of multiple DR types was originally described by Lanzavechia, Sinigallia's and Rothbard's groups. The present study provides a classification of alleles belonging to a main HLA-DR supertype (DR1-4-7-like) which includes DR1, DR2w2a, DR2w2b, DR4w4, DR7, DR9, DR6w19. On the basis data presented herein, at least two additional groups of alleles exist. The first group encodes for molecules with significant, albeit much reduced overlap with the 1-4-7-like supertype (DR4w15, 8w2, 5w11). The second group of alleles (5w12, 3w17, and w53) clearly has little repertoire association with the 1-4-7 supertype. In this context it is interesting to note that Hammer, et al. noted that good DR5w11 binding peptides are frequently characterized by positively charged P6 anchor (which would be poorly compatible) with the herein proposed 1-4-7 supermotif. It is also interesting to note that Sidney, et al. proposed that DR3w17 binds a set of peptides largely distinct from those bound by other common DR types. Future studies will have to determine whether any of the molecules listed above can be grouped in additional DR supertypes. Our group is currently investigating whether analysis of polymorphic residues lining the peptide binding pockets of DR can be utilized to aid in the classification and prediction of HLA DR supertypes.

We would like to comment on similarities and differences between the HLA DR supertype described herein and the recently described HLA class I supermotifs. Class I supermotifs are clear-cut and, as a rule, non-overlapping. Four of them have been described all approximately equally frequent amongst the worldwide population. By contrast, the repertoire defining the HLA DR supertype herein described is not clear-cut and overlaps, at least in part, with the repertoire of other alleles. It also appears that on the basis of the data presented in Tables I and IV, even if other DR supertypes exist, the DR1-4-7 is going to be by far the most abundantly represented worldwide.

Finally, we would like to point out the possible relevance of these data in terms of development of epitope based vaccines. Class II restricted HTL have been implicated in protection from, and termination of many important diseases. Inclusion of well defined class II epitopes in prophylactic or therapeutic vaccines may allow to focus the immune response towards conserved or subdominant epitopes, and avoid suppressive determinants. Based on the data presented herein (Table IV), the DR1-4-7 supertype would allow coverage in the 50 to 80% range, depending on the ethnicities considered. It is thus possible that broad and not ethnically biased population coverage could be achieved by considering a very limited number of peptide binding specificities.

Based on the results present above, the sequences of various antigens of interest were scanned for the presence of the DR 1-4-7 motifs. Peptides identified using this approach are broadly cross reactive, class II restricted T cell epitopes. Table VIII presents a listing of such peptides derived from HBV, HCV, HIV and *Plasmodium falciparum* (*Pf*). A total of 146 peptides were identified: 35 from DHBV, 16 from HCV, 50 from HIV, and 45 from *Pf*. Standard conservancy criteria were employed in applicable cases.

The above examples are provided to illustrate the invention but not to limit its scope. Other variants of the invention will be readily apparent to one of ordinary skill in the art. All publications, patents, and patent applications cited herein are hereby incorporated by reference for all purposes.

TABLE I

HLA-DR binding assays utilized in the present study.

| | | | Representative Assay | | | |
|---|---|---|---|---|---|---|
| Antigen | Allele | Alias | Cell Line | Radiolabeled Probe | Ref. | Comments |
| DR1 | DRB1*0101 | (DR1) | LG2 | HA Y307–319 [1] | (8) | 01 is the most prevalent DR1 allele. |
| DR2 | DRB1*1501 | (DR2w2b) | L466.1 | MBP 88–102Y [2] | (8) | 01 is the most prevalent DR2 allele. |
| DR3 | DRB1*0301 | (DR3w17) | MAT | MT 65kD Y3–13 analog [3] | (8) | 01 is the most prevalent DR3 allele in most major populations. |
| | | | | | | 01 and 02 are approximately equally frequent in North American Blacks. |
| DR4 | DRB1*0401 | (DR4w4) | Preiss | Non-natural peptide YAR [4] | (8) | 01 is the most prevalent DR4 allele in most populations. |
| | DRB1*0405 | (DR4w15) | KT3 | Non-natural peptide YAR | This paper | 05 is the most prevalent DR4 allele in the Orient. |
| DR7 | DRB1*0701 | (DR7) | Pitout | TT 830–843 [5] | (8) | 01/02 vary at only one pos., which is outside the binding groove. |
| DR8 | DRB1*0802 | (DR8w2) | OLL | TT 830–843 | This paper | 02 is dominant in most major population groups. 02 and 03 have nearly identical binding specificities (J. Sidney and A. Sette, see Materials and Methods) |
| DR9 | DRB1*0901 | (DR9) | HID | TT 830–843 | This paper | DR9 alleles are products of a silent mutation. |
| DR11 | DRB1*1101 | (DR5w11) | Sweig | TT 830–843 | (8) | 01 is the most prevalent DR11 allele. |
| DR12 | DRB1*1201 | (DR5w12) | Herluf | C1R derived peptide [6] | (9) | 01/02 are evenly distributed. These alleles differ at pos. 67, which is outside the binding groove and therefore would not be predicted to strongly influence peptide binding. |
| DR13 | DRB1*1302 | (DR6w19) | HO301 | 650.22 (TT 830–843 analog) [7] | (10) | 02 is slightly more prevalent overall than 01. These alleles vary at pos. 86 (critical in determining the P1 anchor specificity). |

TABLE I-continued

HLA-DR binding assays utilized in the present study.

| Antigen | Allele | Alias | Cell Line | Representative Assay Radiolabeled Probe | Ref. | Comments |
|---|---|---|---|---|---|---|
| DR51 | DRB5*0101 | (DR2w2a) | GM3107 | TT 830–843 | (8) | 0101 is the most prevalent allele. |
| DR53 | DRB4*0101 | (DR4, DR7, DR9) | L257.6 | Non-natural peptide YAR [4] | (8) | 0101 is essentially the only allele. |

[1] YPKYVKQNTLKLAT (SEQ ID NO:2)
[2] VVHFFKNIVTPRTPPY (SEQ ID NO:3)
[3] YKTIAFDEEARR (SEQ ID NO:4)
[4] YARFQSQTTLKQKT (SEQ ID NO:5)
[6] EALIHQLKINPYVLS (SEQ ID NO:6)
[7] QYIKANAKFIGITE (SEQ ID NO:7)
[8] Valli et al., 1993.
[9] Falk et al., 1994.

TABLE II

An algorithm to predict DRB1*0401 binding capacity.

| Selection Criteria | High ≤100 | Inter. 100–1000 | Non >1000 | Total |
|---|---|---|---|---|
| \multicolumn{5}{c}{a) Original peptide set.} | | | | |
| None | 27 | 53 | 304 | 384 |
| P1–P6 | 27 | 50 | 182 | 259 |
| −17.00[1] | 27 | 45 | 84 | 156 |
| −16.44[2] | 25 | 35 | 47 | 107 |
| \multicolumn{5}{c}{b) Blind test of the predictive power of the DRB1*0401 algorithm.} | | | | |
| None | 3 | 11 | 36 | 50 |
| P1–P6 | 3 | 9 | 28 | 40 |
| −17.00 | 3 | 8 | 7 | 18 |
| −16.44 | 3 | 4 | 2 | 9 |

No. of peptides (Binding nM)

[1] Algorithm score which predicts 90% of all binders.
[2] Algorithm score which predicts 75% of all binders.

TABLE III

A combined "1-4-7" algorithm.

| Selection Criteria | Degenerate Binders[1] | Percent of Total Degenerate Binders |
|---|---|---|
| None | 73/384 | 100% |
| P1–P6 | 72/259 | 99% |
| Combined Algorithms (90% Cutoff Value) | 67/147 | 92% |
| Combined Algorithms (75% Cutoff Value) | 59/100 | 81% |

[1] Degenerate binders are defined as peptides binding at least two out of the three DR1, 4w4, and 7 molecules with an IC50 of 1 μM or less.

TABLE IV

Phenotypic frequencies of 10 prevalent HLA-DR antigens

| Antigen | Alleles | Cauc. | Blk. | Jpn. | Chn. | Hisp. | Avg. |
|---|---|---|---|---|---|---|---|
| DR1 | DRB1*0101-03 | 18.5 | 8.4 | 10.7 | 4.5 | 10.1 | 10.4 |
| DR2 | DRB1*1501-03 | 19.9 | 14.8 | 30.9 | 22.0 | 15.0 | 20.5 |
| DR3 | DRB1*0301-2 | 17.7 | 19.5 | 0.4 | 7.3 | 14.4 | 11.9 |
| DR4 | DRB1*0401-12 | 23.6 | 6.1 | 40.4 | 21.9 | 29.8 | 24.4 |
| DR7 | DRB1*0701-02 | 26.2 | 11.1 | 1.0 | 15.0 | 16.6 | 14.0 |
| DR8 | DRB1*0801-5 | 5.5 | 10.9 | 25.0 | 10.7 | 23.3 | 15.1 |
| DR9 | DRB1*09011,09012 | 3.6 | 4.7 | 24.5 | 19.9 | 6.7 | 11.9 |
| DR11 | DRB1*1101-05 | 17.0 | 18.0 | 4.9 | 19.4 | 18.1 | 15.5 |
| DR12 | DRB1*1201-02 | 2.8 | 5.5 | 13.1 | 17.6 | 5.7 | 8.9 |
| DR13 | DRB1*1301-06 | 21.7 | 16.5 | 14.6 | 12.2 | 10.5 | 15.1 |
| Total | | 97.0 | 83.9 | 98.8 | 95.5 | 95.6 | 94.7 |

TABLE V

A) Non Predictions.

| | DR1,4,7 | | | Binding Capacity Other Alleles | | | | | | | | | Total Alleles Bound |
|---|---|---|---|---|---|---|---|---|---|---|---|---|---|
| Peptide | DR1 | DR4w4 | DR7 | DR2w2b | DR2w2a | DR3 | DR4w15 | DR5w11 | DR6w19 | DR8w2 | DR9 | DR5w12 | |
| 1136.29 | 32 | 4327 | 138 | 1.1 | 468 | — | 745 | 6250 | — | 2970 | 183 | 1000 | 7 |
| 1136.04 | 24 | 20 | 3333 | 1264 | 741 | — | 563 | 69 | — | 55 | 2885 | — | 6 |
| 1136.19 | 781 | 1915 | 1323 | 86 | 1250 | — | 445 | 183 | 1667 | 5052 | 3125 | — | 4 |

TABLE V-continued

| | | | | | | | | | | | | | |
|---|---|---|---|---|---|---|---|---|---|---|---|---|---|
| 1136.49 | — | — | 505 | — | 702 | — | 250 | 645 | — | 1581 | 4167 | 9091 | 4 |
| 1136.02.01a | 806 | — | — | 2844 | 16 | — | — | 1379 | — | 338 | — | 9927 | 3 |
| 1136.35 | 116 | — | — | 2459 | — | — | 1086 | 126 | 8750 | 306 | — | 1364 | 3 |
| 1136.52 | — | 7031 | 556 | 3957 | 1667 | — | 563 | — | — | — | 2419 | — | 2 |
| 1136.03 | 79 | 8654 | 2033 | 243 | 1250 | — | 1689 | — | — | 7313 | 3947 | 3571 | 2 |
| 1136.06 | 1923 | 1364 | — | — | 313 | 6977 | — | 690 | 8750 | — | — | — | 2 |
| 1136.23 | 962 | — | — | 262 | — | 2727 | — | — | 3182 | — | — | — | 2 |
| 1136.32 | 37 | — | — | 1717 | 1739 | — | 626 | 6250 | — | 1976 | — | — | 2 |
| 1136.33 | 52 | — | — | 8273 | 6250 | — | 7600 | 1835 | 8750 | 3161 | — | 476 | 2 |
| 1136.44.01 | 526 | 780 | — | — | — | — | 6552 | 4000 | — | 6364 | — | — | 2 |
| 1136.62.01a | — | — | — | — | 449 | — | — | 396 | — | 2970 | 3000 | — | 2 |
| 1136.42 | — | 1875 | — | — | 769 | — | — | 9524 | 8750 | — | — | — | 1 |
| 1136.54 | 8333 | — | — | — | — | — | — | — | 761 | — | — | 2727 | 1 |
| 1136.07.01b | 1190 | — | 4630 | 1542 | 2857 | — | — | 1980 | — | 1225 | 2614 | 214 | 1 |
| 1136.05 | — | 492 | — | — | — | — | — | — | — | — | — | — | 1 |
| 1136.08 | — | 9375 | 3788 | 7.3 | — | — | — | — | — | — | 2027 | — | 1 |
| 1136.25 | 1163 | — | 6250 | 28 | 3846 | — | — | — | 2917 | — | — | 3846 | 1 |
| 1136.34 | 4545 | 545 | 3247 | — | — | — | — | — | — | — | 5000 | — | 1 |
| 1136.36 | 204 | — | — | 5688 | — | — | — | — | — | — | 12931 | — | 1 |
| 1136.64 | — | 225 | — | — | — | — | 1267 | — | 5000 | — | — | — | 1 |
| 1136.69 | — | — | — | — | — | — | — | — | 54 | — | 5769 | — | 1 |
| 1136.40 | 4545 | 1546 | 8333 | — | 4348 | — | — | — | 7000 | — | — | — | 0 |
| 1136.50 | — | 1875 | — | — | — | — | 6667 | 7143 | — | 5506 | — | — | 0 |
| 1136.56 | — | 4500 | — | — | — | — | 3918 | — | 3500 | — | — | — | 0 |
| 1136.57 | — | 8654 | — | 6500 | — | — | 5758 | 1626 | — | 5104 | 4688 | — | 0 |
| 1136.61 | — | — | — | — | — | — | — | — | — | — | 7979 | — | 0 |
| 1136.66 | — | — | — | — | — | — | — | — | — | — | — | — | 0 |
| 1136.68 | — | — | — | — | — | — | — | — | — | — | — | — | 0 |
| 1136.70 | — | — | — | — | — | — | — | 3704 | — | — | — | — | 0 |
| 1136.72 | — | — | — | — | — | — | — | — | — | — | — | — | 0 |
| 1136.63.01a | — | — | — | — | 1905 | — | — | 7692 | — | 4298 | — | — | 0 |

2 out of 34 (5.9%) degenerate on 5 or more DR types.

B) Correct Predictions.

| Peptide | Binding Capacity (IC50% nM) | | | | | | | | | | | | Total Alleles Bound |
|---|---|---|---|---|---|---|---|---|---|---|---|---|---|
| | DR1,4,7 | | | Other Alleles | | | | | | | | | |
| | DR1 | DR4w4 | DR7 | DR2w2b | DR2w2a | DR3 | DR4w15 | DR5w11 | DR6w19 | DR8w2 | DR9 | DR5w12 | |
| 1188.16 | 3.7 | 7.1 | 14 | 1251 | 23 | — | 47 | 30 | 428 | 46 | 28 | — | 9 |
| 1188.32 | 3.1 | 44 | 167 | — | 29 | — | 1402 | 11 | 7.1 | 19 | 126 | 851 | 9 |
| 1188.34 | 14 | 12 | 66 | 370 | 148 | 1332 | 959 | 2703 | 3.7 | 68 | 19 | 497 | 9 |
| F107.09 | 4.1 | 14 | 39 | 5028 | 286 | — | 324 | 963 | 469 | 385 | 29 | — | 9 |
| 27.412 | 14 | 282 | 138 | — | 323 | — | — | 31 | 20 | 53 | 590 | 2495 | 8 |
| 1188.45 | 26 | 9.0 | 57 | 260 | 123 | 757 | 1057 | 2532 | 3.9 | 28 | 16 | — | 8 |
| 1136.16 | 1.6 | 214 | 46 | 1625 | 34 | — | 741 | 3571 | 1296 | 488 | 68 | 3409 | 7 |
| 1136.21 | 2.2 | 51 | 52 | 2844 | 62 | — | 270 | 1212 | 259 | 1420 | 132 | — | 7 |
| 1136.11 | 0.89 | 99 | 9615 | 603 | 261 | — | 84 | 315 | — | 529 | 1974 | — | 7 |
| 27.392 | 41 | 449 | 33 | 310 | 2499 | — | 1668 | 1203 | 9.8 | 883 | 62 | — | 6 |
| 27.417 | 56 | — | 425 | 210 | 251 | — | — | 471 | 33 | 2177 | 859 | 3243 | 6 |
| 1136.38 | 70 | 122 | 2404 | 258 | 741 | — | 133 | 4000 | 1842 | — | 862 | — | 6 |
| 27.388 | 50 | 5737 | 497 | 18 | 1536 | — | 1410 | 542 | 38 | — | 708 | 2512 | 5 |
| 27.403 | 78 | 4146 | 207 | 13 | 2875 | — | — | 73 | 66 | 1672 | 423 | 7321 | 5 |
| 1136.71 | 5.1 | 776 | 96 | — | 1212 | — | 950 | 1538 | — | — | 375 | — | 5 |
| 1136.14 | 5.3 | 4787 | 100 | 81 | 135 | — | 792 | — | 1400 | — | 7732 | 3488 | 5 |
| 1136.24 | 182 | 5844 | 391 | 506 | 9524 | — | 1357 | — | 6.5 | — | — | — | 4 |
| 27.384 | 66 | — | 281 | 357 | — | — | — | — | 65 | — | 458 | — | 4 |
| 1188.13 | 116 | 6923 | 58 | 382 | — | — | 1069 | — | 0.77 | — | 142 | — | 4 |
| F107.10 | 120 | 2728 | 67 | 807 | — | — | 1647 | — | 5.5 | — | 135 | — | 4 |
| F107.17 | 221 | 388 | — | — | — | 4878 | 5705 | — | 76 | 7640 | 299 | 3478 | 4 |
| F107.23 | 163 | 5713 | 141 | 4413 | — | — | 6770 | — | 14 | — | 151 | — | 4 |
| 1136.12 | 105 | 720 | 1429 | 14 | 2128 | — | 1583 | — | 343 | 2917 | 2500 | — | 4 |
| 1136.47 | 2.2 | 407 | 2119 | 303 | 755 | — | 5352 | 4255 | — | — | — | — | 4 |
| 1136.28 | 0.23 | 849 | 3623 | 2.2 | 1481 | — | 6667 | 9524 | 3182 | 7538 | — | 4478 | 3 |
| 1136.55 | 65 | 138 | 2451 | — | — | — | 271 | 4545 | 5000 | — | — | — | 3 |
| 1136.59.01a | 130 | 39 | — | — | 29 | — | 3140 | — | — | — | — | — | 3 |
| 27.415 | 2011 | 754 | 718 | 653 | — | — | — | 6712 | 2234 | 8997 | — | — | 2 |
| 1136.46 | 68 | 985 | 5814 | — | — | — | — | — | — | — | — | — | 2 |

16 out of 29 (55%) degenerate on 5 or more DR types.
—Indicates binding affinity ≧10,000 nM.

TABLE VI

Degenerate "1-4-7" binders.

| Peptide | Sequence | SEQ ID NO. | Binding Capacity (IC 50% nM) | | | | | | | |
|---|---|---|---|---|---|---|---|---|---|---|
| | | | DR1,4,7 | | | Other Alleles | | | | |
| | | | DRB1 | DR4w4 | DR7 | DR2w2b | DR2w2a | DR3 | DR4w15 | DR5w11 |
| 1188.34 | HNWVNHAVPLAMKLI | 8 | + | + | + | + | + | − | + | − |
| 1188.32 | GLAYKFVVPGAATPY | 9 | + | + | + | − | + | − | − | + |
| 1188.16 | KSKYKLATSVLAGLL | 10 | + | + | + | − | + | − | + | + |
| F107.09 | KYKLATSVLAGLLGN | 11 | + | + | + | − | + | − | + | + |
| 1188.45 | RHNWVNHAVPLAMKL | 12 | + | + | + | + | + | + | − | − |
| 27.412 | AYKFVVPGAATPYAG | 13 | + | + | + | − | + | − | − | + |
| 1136.11 | VVFPASFFIKLPIILA | 14 | + | + | − | + | + | − | + | + |
| 1136.16 | LTSQFFLPALPVFTWL | 15 | + | + | + | − | + | − | + | − |
| 1136.21 | IPQEWKPAITVKVLPA | 16 | + | + | + | − | + | − | + | − |
| 1136.29 | GPPTALRSFGFAFGYM | 17 | + | − | + | + | + | − | + | − |
| 27.392 | SSVFNVVNSSIGLIM | 18 | + | + | + | + | − | − | − | − |
| 27.417 | VKNVIGPFMKAVCVE | 19 | + | − | + | + | + | − | − | + |
| 1136.04 | LFHYYFLSEKAPGSTV | 20 | + | + | − | − | + | − | + | + |
| 27.388 | MRKLAILSVSSFLFV | 21 | + | − | + | + | − | − | − | + |
| 1136.38 | SSIIFGAFPSLHSGCC | 22 | + | + | − | + | + | − | + | − |
| 27.403 | LVNLLIFHINGKIIK | 23 | + | − | + | + | − | − | − | + |
| 1136.71 | EPQGSTYAASSATSVD | 24 | + | + | + | − | − | − | + | − |
| 1136.14 | FATCFLIPLTSQFFLP | 25 | + | − | + | + | + | − | + | − |
| 27.384 | FNVVNSSIGLIMVLS | 26 | + | − | + | + | − | − | − | − |
| 1188.13 | AGLLGNVSTVLLGGV | 27 | + | − | + | + | − | − | − | − |
| F107.10 | LAGLLGNVSTVLLGG | 28 | + | − | + | + | − | − | − | − |
| 1136.47 | THHYFVDLIGGAMLSL | 29 | + | + | − | + | + | − | − | − |
| 1136.12 | IKLPIILAFATCFLIP | 30 | + | + | − | + | − | − | − | − |
| F107.23 | VFNVVNSSIGLIMVL | 31 | + | − | + | − | − | − | − | − |
| 1136.24 | NLSNVLATITTGVLDI | 32 | + | − | + | + | − | − | − | − |
| F107.17 | KFVVPGAATPYAGEP | 33 | + | + | − | − | − | − | − | − |
| 1136.28 | LAAIIFLFGPPTALRS | 34 | + | + | − | + | − | − | − | − |
| 1136.55 | QEIDPLSYNYIPVNSN | 35 | + | + | − | − | − | − | + | − |
| 1136.59.01a | RVYQEPQVSPPQRAET | 36 | + | + | − | − | + | − | − | − |
| 27.415 | NVKYLVIVFLIFFDL | 37 | − | + | + | + | − | − | − | − |
| 1136.46 | LWWSTMYLTHHYFVDL | 38 | + | + | − | − | − | − | − | − |
| 1136.44.01 | WLFPRFKFVWVTYASW | 39 | + | + | − | − | − | − | − | − |
| | | | 31 | 22 | 21 | 18 | 16 | 1 | 12 | 9 |

| Peptide | Sequence | SEQ ID NO. | Binding Capacity (IC 50% nM) | | | | Total Alleles Bound |
|---|---|---|---|---|---|---|---|
| | | | Other Alleles | | | | |
| | | | DR6w19 | DR8w2 | DR9 | DR5w12 | |
| 1188.34 | HNWVNHAVPLAMKLI | 8 | + | + | + | + | 10 |
| 1188.32 | GLAYKFVVPGAATPY | 9 | + | + | + | + | 9 |
| 1188.16 | KSKYKLATSVLAGLL | 10 | + | + | + | − | 9 |
| F107.09 | KYKLATSVLAGLLGN | 11 | + | + | + | − | 9 |
| 1188.45 | RHNWVNHAVPLAMKL | 12 | + | + | + | − | 9 |
| 27.412 | AYKFVVPGAATPYAG | 13 | + | + | + | − | 8 |
| 1136.11 | VVFPASFFIKLPIILA | 14 | − | + | − | − | 7 |
| 1136.16 | LTSQFFLPALPVFTWL | 15 | − | + | + | − | 7 |
| 1136.21 | IPQEWKPAITVKVLPA | 16 | + | − | + | − | 7 |
| 1136.29 | GPPTALRSFGFAFGYM | 17 | − | − | + | + | 7 |
| 27.392 | SSVFNVVNSSIGLIM | 18 | + | + | + | − | 7 |
| 27.417 | VKNVIGPFMKAVCVE | 19 | + | − | + | − | 7 |
| 1136.04 | LFHYYFLSEKAPGSTV | 20 | − | + | − | − | 6 |
| 27.388 | MRKLAILSVSSFLFV | 21 | + | − | + | − | 6 |
| 1136.38 | SSIIFGAFPSLHSGCC | 22 | − | − | + | − | 6 |
| 27.403 | LVNLLIFHINGKIIK | 23 | + | − | + | − | 6 |
| 1136.71 | EPQGSTYAASSATSVD | 24 | − | − | + | − | 5 |
| 1136.14 | FATCFLIPLTSQFFLP | 25 | − | − | − | − | 5 |
| 27.384 | FNVVNSSIGLIMVLS | 26 | + | − | + | − | 5 |
| 1188.13 | AGLLGNVSTVLLGGV | 27 | + | − | + | − | 5 |
| F107.10 | LAGLLGNVSTVLLGG | 28 | + | − | + | − | 5 |
| 1136.47 | THHYFVDLIGGAMLSL | 29 | − | − | − | − | 4 |
| 1136.12 | IKLPIILAFATCFLIP | 30 | + | − | − | − | 4 |
| F107.23 | VFNVVNSSIGLIMVL | 31 | + | − | + | − | 4 |
| 1136.24 | NLSNVLATITTGVLDI | 32 | + | − | − | − | 4 |
| F107.17 | KFVVPGAATPYAGEP | 33 | + | − | + | − | 4 |
| 1136.28 | LAAIIFLFGPPTALRS | 34 | − | − | − | − | 3 |
| 1136.55 | QEIDPLSYNYIPVNSN | 35 | − | − | − | − | 3 |
| 1136.59.01a | RVYQEPQVSPPQRAET | 36 | − | − | − | − | 3 |
| 27.415 | NVKYLVIVFLIFFDL | 37 | − | − | − | − | 3 |

TABLE VI-continued

Degenerate "1-4-7" binders.

| | | | | | | | |
|---|---|---|---|---|---|---|---|
| 1136.46 | LWWSTMYLTHHYFVDL | 38 | – | – | – | – | 2 |
| 1136.44.01 | WLFPRFKFVWVTYASW | 39 | – | – | – | – | 2 |
| | | | 18 | 10 | 20 | 3 | |

+ indicates binding affinity (IC 50%)$^2$ 1000 nM.

TABLE VII

| | Frequency of Binders | |
|---|---|---|
| DR Type | 1-4-7 Degenerate Binders (%) | Non 1-4-7 Degenerate Binders (%) |
| 1 | 31/32 (97) | 17/67 (25) |
| 4w4 | 22/32 (69) | 8/67 (12) |
| 7 | 21/32 (66) | 7/67 (10) |
| 9 | 20/32 (62) | 2/67 (3.0) |
| 6w19 | 18/32 (56) | 6/67 (8.9) |
| 2w2βb | 18/32 (56) | 16/67 (24) |
| 2w2βa | 16/32 (50) | 10/67 (15) |
| 4w15 | 12/32 (37) | 4/67 (6.0) |
| 8w2 | 10/32 (31) | 3/67 (4.5) |
| 5w11 | 9/32 (28) | 6/67 (8.9) |
| 5w12 | 3/32 (9.4) | 4/67 (6.0) |
| 3w17 | 1/32 (3.1) | 0/67 (0) |
| w53 | 2/16 (13) | 7/43 (16) |

TABLE VIII

| Sequence | SEQ ID NO: | Source | 1st Pos | Conservancy | Predicted 1-4-7 |
|---|---|---|---|---|---|
| IGPFMKAVCVEVEKT | 40 | Pf TRAP | 227 | 100 | 3 |
| ILSVFFLALFFIIFN | 41 | Pf EXP1 | 3 | | 3 |
| KSKYKLATSVLAGLL | 42 | Pf EXP1 | 71 | | 3 |
| KYKLATSVLAGLLGN | 43 | Pf EXP1 | 73 | | 3 |
| LGNVKYLVIVFLIFF | 44 | Pf TRAP | 4 | 100 | 3 |
| LSVFFLALFFIIFNK | 45 | Pf EXP1 | 4 | | 3 |
| LVNLLIFHINGKIIK | 46 | Pf LSA1 | 13 | | 3 |
| MKILSVFFLALFFII | 47 | Pf EXP1 | 1 | | 3 |
| MRKLAILSVSSFLFV | 48 | Pf CSP | 2 | 95 | 3 |
| NSSIGLIMVLSFLFL | 49 | Pf CSP | 417 | 95 | 3 |
| NVKYLVIVFLIFFDL | 50 | Pf TRAP | 6 | 100 | 3 |
| SFYFILVNLLIFHIN | 51 | Pf LSA1 | 8 | | 3 |
| VFFLALFFIIFNKES | 52 | Pf EXP1 | 6 | | 3 |
| YFILVNLLIFHINGK | 53 | Pf LSA1 | 10 | | 3 |
| YISFYFILVNLLIFH | 54 | Pf LSA1 | 6 | | 3 |
| AGLLGNVSTVLLGGV | 55 | Pf EXP1 | 82 | | 2 |
| ANQLVVILTDGIPDS | 56 | Pf TRAP | 153 | 100 | 2 |
| AYKFVVPGAATPYAG | 57 | Pf TRAP | 514 | 80 | 2 |
| DKELTMSNVKNVSQT | 58 | Pf LSA1 | 81 | | 2 |
| FNVVNSSIGLIMVLS | 59 | Pf CSP | 413 | 100 | 2 |
| FYFILVNLLIFHING | 60 | Pf LSA1 | 9 | | 2 |
| GLAYKFVVPGAATPY | 61 | Pf TRAP | 512 | 80 | 2 |
| GRDVQNNIVDEIKYR | 62 | Pf TRAP | 25 | 90 | 2 |
| HILYISFYFILVNLL | 63 | Pf LSA1 | 3 | | 2 |
| HNWVNHAVPLAMKLI | 64 | Pf TRAP | 62 | 80 | 2 |
| IVFLIFFDLFLVNGR | 65 | Pf TRAP | 12 | 100 | 2 |
| KFVVPGAATPYAGEP | 66 | Pf TRAP | 516 | 80 | 2 |
| KSLLRNLGVSENIFL | 67 | Pf LSA1 | 98 | | 2 |
| KYLVIVFLIFFDLFL | 68 | Pf TRAP | 8 | 100 | 2 |
| LAGLLGNVSTVLLGG | 69 | Pf EXP1 | 81 | | 2 |
| LGNVSTVLLGGVGLV | 70 | Pf EXP1 | 85 | | 2 |
| LIFFDLFLVNGRDVQ | 71 | Pf TRAP | 15 | 100 | 2 |
| LVVILTDGIPDSIQD | 72 | Pf TRAP | 156 | 100 | 2 |
| QLVVILTDGIPDSIQ | 73 | Pf TRAP | 155 | 100 | 2 |
| RGYYIPHQSSLPQDN | 74 | Pf LSA1 | 1669 | | 2 |
| RHNWVNHAVPLAMKL | 75 | Pf TRAP | 61 | 80 | 2 |
| RHPFKIGSSDPADNA | 76 | Pf EXP1 | 107 | | 2 |
| SSVFNVVNSSIGLIM | 77 | Pf CSP | 410 | 95 | 2 |
| VFNVVNSSIGLIMVL | 78 | Pf CSPF | 412 | 95 | 2 |
| VKNVIGPFMKAVCVE | 79 | Pf TRAP | 223 | 100 | 2 |
| VKYLVIVFLIFFDLF | 80 | Pf TRAP | 7 | 100 | 2 |

TABLE VIII-continued

| | | | | | |
|---|---|---|---|---|---|
| VSTVLLGGVGLVLYN | 81 | Pf EXP1 | 88 | | 2 |
| WENVKNVIGPFMKAV | 82 | Pf TRAP | 220 | 100 | 2 |
| YKFVVPGAATPYAGE | 83 | Pf TRAP | 515 | 80 | 2 |
| ENRWQVMIVWQVDRM | 84 | HIV1 VIF | 2 | 81 | 3 |
| ERYLKDQQLLGIWGCS | 85 | HIV1 ENV | 589 | | 3 |
| ESELVSQIIEQLIKK | 86 | HIV1 POL | 696 | 80 | 3 |
| FRKYTAFTIPSINNE | 87 | HIV1 POL | 303 | 93 | 3 |
| GQMVHQAISPRTLNA | 88 | HIV1 GAG | 172 | 88 | 3 |
| IPEWEFVNTPPLVKL | 89 | HIV1 POL | 593 | 93 | 3 |
| LPPVVAKEIVASCDK | 90 | HIV1 POL | 770 | 87 | 3 |
| NREILKEPVHGVYYD | 91 | HIV1 POL | 485 | 87 | 3 |
| PAIFQSSMTKILEPF | 92 | HIV1 POL | 336 | 80 | 3 |
| PPVVAKEIVASCDKC | 93 | HIV1 POL | 771 | 87 | 3 |
| QEQIGWMTNNPPIPV | 94 | HIV1 GAG | 276 | 81 | 3 |
| QGQMVHQAISPRTLN | 95 | HIV1 GAG | 171 | 85 | 3 |
| SPAIFQSSMTKILEP | 96 | HIV1 POL | 335 | 80 | 3 |
| TLNFPISPIETVPVK | 97 | HIV1 POL | 176 | 100 | 3 |
| VKNWMTETLLVQNAN | 98 | HIV1 GAG | 348 | 81 | 3 |
| VPVWKEATTTLFCAS | 99 | HIV1 ENV | 54 | 81 | 3 |
| WEFVNTPPLVKLWYQ | 100 | HIV1 POL | 596 | 93 | 3 |
| WVKVVEEKAFSPEVI | 101 | HIV GAG | 187 | 33 | 3 |
| YYGVPVWKEATTTLF | 102 | HIV1 ENV | 51 | 83 | 3 |
| ASDFNLPPVVAKEIV | 103 | HIV1 POL | 765 | 80 | 2 |
| ASGYIEAEVIPAETG | 104 | HIV1 POL | 822 | 93 | 2 |
| DFNLPPVVAKEIVAS | 105 | HIV1 POL | 767 | 87 | 2 |
| EAIIRILQQLLFIHF | 106 | HIV1 VPR | 58 | 82 | 2 |
| EKVYLAWVPAHKGIG | 107 | HIV1 POL | 711 | 93 | 2 |
| ETAYFLLKLAGRWPV | 108 | HIV POL | 838 | 65 | 2 |
| EVQLGIPHPAGLKKK | 109 | HIV1 POL | 268 | 80 | 2 |
| FWEVQLGIPHPAGLK | 110 | HIV1 POL | 266 | 100 | 2 |
| GCTLNFPISPIETVP | 111 | HIV1 POL | 174 | 100 | 2 |
| GEIYKRWIILGLNKI | 112 | HIV1 GAG | 294 | 85 | 2 |
| GTVLVGPTPVNIIGR | 113 | HIV1 POL | 153 | 100 | 2 |
| HKAIGTVLVGPTPVN | 114 | HIV1 POL | 149 | 93 | 2 |
| IGTVLVGPTPVNIIG | 115 | HIV POL | 152 | 74 | 2 |
| KRWIILGLNKIVRMY | 116 | HIV1 GAG | 298 | 88 | 2 |
| KVYLAWVPAHKGIGG | 117 | HIV POL | 712 | 74 | 2 |
| LICTTAVPWNASWSNK | 118 | HIV1 ENV | 607 | | 2 |
| LLQLTVWGIKQLQAR | 119 | HIV1 ENV | 731 | 80 | 2 |
| NFPISPIETVPVKLK | 120 | HIV1 POL | 178 | 100 | 2 |
| PQGWKGSPAIFQSSM | 121 | HIV1 POL | 329 | 87 | 2 |
| PVNIIGRNLLTQIGC | 122 | HIV1 POL | 161 | 87 | 2 |
| QHLLQLTVWGIKQLQ | 123 | HIV1 ENV | 729 | 80 | 2 |
| QQHLLQLTVWGIKQL | 124 | HIV1 ENV | 728 | 80 | 2 |
| SPEVIPMFSALSEGA | 125 | HIV1 GAG | 197 | 88 | 2 |
| TKELQKQITKIQNFR | 126 | HIV POL | 952 | 67 | 2 |
| TVLVGPTPVNIIGRN | 127 | HIV1 POL | 154 | 100 | 2 |
| VEAIIRILQQLLFIH | 128 | HIV1 VPR | 57 | 82 | 2 |
| VIPMFSALSEGATPQ | 129 | HIV1 GAG | 200 | 88 | 2 |
| VNIIGRNLLTQIGCT | 130 | HIV1 POL | 162 | 87 | 2 |
| WGCSGKLICTTAVPWN | 131 | HIV1 ENV | 601 | | 2 |
| WIILGLNKIVRMYSP | 132 | HIV1 GAG | 300 | 88 | 2 |
| YKRWIILGLNKIVRM | 133 | HIV1 GAG | 297 | 88 | 2 |
| FILVNLLIFHINGKI | 134 | Pf LSA1 | 11 | | 3 |
| AEDLNLGNLNVSIPW | 135 | HBV POL | 38 | 95 | 3 |
| DLNLGNLNVSIPWTH | 136 | HBV POL | 40 | 95 | 3 |
| GFFLLTRILTIPQSL | 137 | HBV ENV | 181 | 80 | 3 |
| IFLFILLLCLIFLLV | 138 | HBV ENV | 245 | 80 | 3 |
| NLNVSIPWTHKVGNF | 139 | HBV POL | 45 | 95 | 3 |
| PFLLAQFTSAICSVV | 140 | HBV POL | 523 | 95 | 3 |
| RFSWLSLLVPFVQWF | 141 | HBV ENV | 332 | 100 | 3 |
| SPFLLAQFTSAICSV | 142 | HBV POL | 522 | 95 | 3 |
| SVRFSWLSLLVPFVQ | 143 | HBV ENV | 330 | 80 | 3 |
| AFSYMDDVVLGAKSV | 144 | HBV POL | 546 | 90 | 2 |
| AGFFLLTRILTIPQS | 145 | HBV ENV | 180 | 80 | 2 |
| FVQWFVGLSPTVWLS | 146 | HBV ENV | 342 | 95 | 2 |
| GAHLSLRGLPVCAFS | 147 | HBV X | 50 | 90 | 2 |
| GTSFVYVPSALNPAD | 148 | HBV POL | 774 | 80 | 2 |
| GVWIRTPPAYRPPNA | 149 | HBV NUC | 123 | 95 | 2 |
| HLSLRGLPVCAFSSA | 150 | HBV X | 52 | 90 | 2 |
| IIFLFILLLCLIFLL | 151 | HBV ENV | 244 | 80 | 2 |
| ILLLCLIFLLVLLDY | 152 | HBV ENV | 249 | 95 | 2 |
| IVGLLGFAAPFTQCG | 153 | HBV POL | 636 | 90 | 2 |
| KFAVPNLQSLTNLLS | 154 | HBV POL | 406 | 95 | 2 |
| LAQFTSAICSVVRRA | 155 | HBV POL | 526 | 95 | 2 |
| LCLIFLLVLLDYQGM | 156 | HBV ENV | 252 | 95 | 2 |
| LCQVFADATPTGWGL | 157 | HBV POL | 694 | 95 | 2 |
| LHLYSHPIILGFRKI | 158 | HBV POL | 501 | 80 | 2 |
| LLCLIFLLVLLDYQG | 159 | HBV ENV | 251 | 95 | 2 |

TABLE VIII-continued

| Sequences | SEQ ID NO: | Source | Peptide | AA | |
|---|---|---|---|---|---|
| LVLLDYQGMLPVCPL | 160 | HBV ENV | 258 | 90 | 2 |
| LVPFVQWFVGLSPTV | 161 | HBV ENV | 339 | 95 | 2 |
| PLPIHTAELLAACFA | 162 | HBV POL | 722 | 80 | 2 |
| QCGYPALMPLYACIQ | 163 | HBV POL | 648 | 95 | 2 |
| RDLLDTASALYREAL | 164 | HBV NUC | 28 | 80 | 2 |
| SFGVWIRTPPAYRPP | 165 | HBV NUC | 121 | 90 | 2 |
| SVVLSRKYTSFPWLL | 166 | HBV POL | 750 | 85 | 2 |
| VGLLGFAAPFTQCGY | 167 | HBV POL | 637 | 95 | 2 |
| VPNLQSLTNLLSSNL | 168 | HBV POL | 409 | 85 | 2 |
| WPKFAVPNLQSLTNL | 169 | HBV POL | 404 | 95 | 2 |
| KVLVLNPSVAATLGF | 170 | HCV | 1255 | 100 | 3 |
| PTLWARMILMTHFFS | 171 | HCV | 2870 | 79 | 3 |
| ADLMGYIPLVGAPLG | 172 | HCV | 131 | 79 | 2 |
| AVQWMNRLIAFASRG | 173 | HCV | 1917 | 100 | 2 |
| DLELITSCSSNVSVA | 174 | HCV | 2812 | 93 | 2 |
| DLYLVTRHADVIPVR | 175 | HCV | 1134 | 79 | 2 |
| EDLVNLLPAILSPGA | 176 | HCV | 1882 | 79 | 2 |
| FTTLPALSTGLIHLH | 177 | HCV | 684 | 79 | 2 |
| GARLVVLATATPPGS | 178 | HCV | 1345 | 79 | 2 |
| GIQYLAGLSTLPGNP | 179 | HCV | 1776 | 100 | 2 |
| GVNYATGNLPGCSFS | 180 | HCV | 161 | 79 | 2 |
| IQYLAGLSTLPGNPA | 181 | HCV | 1777 | 100 | 2 |
| LHGLSAFSLHSYSPG | 182 | HCV | 2919 | 79 | 2 |
| VNLLPAILSPGALVV | 183 | HCV | 1885 | 79 | 2 |
| VQWMNRLIAFASRGN | 184 | HCV | 1918 | 100 | 2 |
| YKVLVLNPSVAATLG | 185 | HCV | 1254 | 100 | 2 |

Class II Peptides

| Sequences | SEQ ID NO: | Source | Peptide | AA |
|---|---|---|---|---|
| SALLSSDITASVNCAK | 186 | HEL 81–96 | 008.00 | 16 |
| SALSEGATPQDLNTML | 187 | HIV gp25 41–56 | 200.06 | 16 |
| NKALELFRKDIAAKYK | 188 | Sp. W. myo. 132–147 | 213.10 | 16 |
| NKALELFRKDIAAKYKELGY | 189 | SW Myo 132–151 | 506.01 | 20 |
| ALELFRKDIAAKYKELGY | 190 | Sp. W myo. 134–151 | 506.03 | 18 |
| ELFRKDIAAKYKELGY | 191 | Sp. W myo. 136–151 | 506.05 | 16 |
| MAKTIAYDEEARRGLE | 192 | Heat Shock Prot | 570.01 | 16 |
| KVYLPRMKMEEKYNLTSVLM | 193 | Ova 279–298 | 705.06 | 20 |
| YASFVKTTTLRKFT-NH2 | 194 | combinatorial; DR2 optimized | 717.04 | 14 |
| PHHTALRQAILCWGELMTLA | 195 | HBV.core.50 | 857.02 | 20 |
| YKMKMVHAAHAKMKM | 196 | OVA KM core extension | 865.01 | 15 |
| GFYTTGAVRQIFGDYKTTIC | 197 | PLP 91–110 | F050.03 | 20 |
| QNILLSNAPLGPQFP | 198 | Tyrosinase 56–70 | F089.01 | 15 |
| AAYAAQGYKVLVLNPSVAAT | 199 | HCV NS3 1242–1261 | F098.03 | 20 |
| GYKVLVLNPSVAATLGFGAY | 200 | HCV NS3 1248–1267 | F098.04 | 20 |
| GYKVLVLNPSVAAT | 201 | HCV NS3 1248–1261 | F098.05 | 14 |
| SYVNTNMGLKFRQLLWFHI | 202 | HBV Core 87–105 | F098.06 | 19 |
| GLKFRQLLWFHI | 203 | HBV Core 94–105 | F098.10 | 12 |
| TLHGPTPLLYRLGAVQNEIT | 204 | HCV NS4 1–20 | F134.04 | 20 |
| NFISGIQYLAGLSTLPGNPA | 205 | HCV.NS4.151 | F134.05 | 20 |
| GEGAVQWMNRLIAFASRGNHV | 206 | HCV.NS4.293.(1914–1934) | F134.08 | 21 |
| KPVSQMRMATPLLMRPM | 207 | Mouse invariant chain 85–101 | 1A-p5 | 17 |
| LPKPPKPVSKMRMATPLLMQALPM | 208 | Human invariant chain 80–103 | Tr-28 p1 | 24 |
| EYLVSFGVWIRTPPA | 209 | HBV.nuc.117 | 27.0279 | 15 |
| GVWIRTPPAYRPPNA | 149 | HBV.nuc.123 | 27.0280 | 15 |
| RHYLHTLWKAGILYK | 210 | HBV.pol.145 | 27.0281 | 15 |
| VPNLQSLTNLLSSNL | 168 | HBV POL 409 | 27.0283 | 15 |
| WVTVYYGVPVWKEAT | 211 | HIV1.env.47 | 27.0288 | 15 |
| YYGVPVWKEATTTLF | 102 | HIV1 ENV 51 | 27.0293 | 15 |
| VPVWKEATTTLFCAS | 99 | HIV1.env.54 | 27.0294 | 15 |
| LSGIVQQQNNLLRAI | 212 | HIV1.env.711 | 27.0295 | 15 |
| QQHLLQLTVWGIKQL | 124 | HIV1 ENV 728 | 27.0296 | 15 |
| QHLLQLTVWGIKQLQ | 123 | HIV1.env.729 | 27.0297 | 15 |
| LLQLTVWGIKQLQAR | 119 | HIV1 ENV 731 | 27.0298 | 15 |
| QGQMVHQAISPRTLN | 95 | HIV1.gag.171 | 27.0304 | 15 |
| SPEVIPMFSALSEGA | 125 | HIV1 GAG 197 | 27.0307 | 15 |
| QEQIGWMTNNPPIPV | 94 | HIV1 GAG 276 | 27.0310 | 15 |
| GEIYKRWIILGLNKI | 112 | HIV1.gag.294 | 27.0311 | 15 |
| YKRWIILGLNKIVRM | 133 | HIV1 GAG 297 | 27.0312 | 15 |
| KRWIILGLNKIVRMY | 116 | HIV1.gag.298 | 27.0313 | 15 |
| WIILGLNKIVRMYSP | 132 | HIV1.gag.300 | 27.0314 | 15 |
| VKNWMTETLLVQNAN | 98 | HIV1 GAG 348 | 27.0315 | 15 |
| GTVLVGPTPVNIIGR | 113 | HIV1 POL 153 | 27.0322 | 15 |

TABLE VIII-continued

| | | | | |
|---|---|---|---|---|
| PVNIIGRNLLTQIGC | 122 | HIV1 POL 161 | 27.0324 | 15 |
| GRNLLTQIGCTLNFP | 213 | HIV1.pol.166 | 27.0326 | 15 |
| TLNFPISPIETVPVK | 97 | HIV1 POL 176 | 27.0328 | 15 |
| NFPISPIETVPVKLK | 120 | HIV1.pol.178 | 27.0329 | 15 |
| FRKYTAFTIPSINNE | 87 | HIV1.pol.303 | 27.0341 | 15 |
| SPAIFQSSMTKILEP | 96 | HIV1.pol.335 | 27.0344 | 15 |
| PAIFQSSMTKILEPF | 92 | HIV1 POL 336 | 27.0345 | 15 |
| QKLVGKLNWASQIYA | 214 | HIV1 POL 437 | 27.0349 | 15 |
| VGKLNWASQIYAGIK | 215 | HIV1.pol.440 | 27.0350 | 15 |
| NREILKEPVHGVYYD | 91 | HIV1.pol.485 | 27.0351 | 15 |
| IPEWEFVNTPPLVKL | 89 | HIV1 POL 593 | 27.0353 | 15 |
| WEFVNTPPLVKLWYQ | 100 | HIV1.pol.596 | 27.0354 | 15 |
| EQLIKKEKVYLAWVP | 216 | HIV1 POL 705 | 27.0360 | 15 |
| EKVYLAWVPAHKGIG | 107 | HIV1.pol.711 | 27.0361 | 15 |
| HSNWRAMASDFNLPP | 217 | HIV1.pol.758 | 27.0364 | 15 |
| ASGYIEAEVIPAETG | 104 | HIV1 POL 822 | 27.0370 | 15 |
| AEHLKTAVQMAVFIH | 218 | HIV1.pol.911 | 27.0372 | 15 |
| KTAVQMAVFIHNFKR | 219 | HIV1.pol.915 | 27.0373 | 15 |
| QKQITKIQNFRVYYR | 220 | HIV1.pol.956 | 27.0377 | 15 |
| KLLWKGEGAVVIQDN | 221 | HIV1.pol.982 | 27.0379 | 15 |
| ENRWQVMIVWQVDRM | 84 | HIV1.vif.2 | 27.0381 | 15 |
| VEAIIRILQQLLFIH | 128 | HIV1 VPR 57 | 27.0382 | 15 |
| FNVVNSSIGLIMVLS | 59 | Pf CSP 413 | 27.0384 | 15 |
| MNYYGKQENWYSLKK | 222 | Pf CSP 53 | 27.0387 | 15 |
| MRKLAILSVSSFLFV | 48 | Pf.CSP.2 | 27.0388 | 15 |
| NSSIGLIMVLSFLFL | 49 | Pf CSP 417 | 27.0390 | 15 |
| SSVFNVVNSSIGLIM | 77 | Pf.CSP.410 | 27.0392 | 15 |
| MKILSVFFLALFFII | 47 | Pf EXP1 1 | 27.0393 | 15 |
| FILVNLLIFHINGKI | 134 | Pf LSA1 11 | 27.0398 | 15 |
| HILYISFYFILVNLL | 63 | Pf LSA1 3 | 27.0400 | 15 |
| LLIFHINGKIIKNSE | 223 | Pf LSA1 16 | 27.0402 | 15 |
| LVNLLIFHINGKIIK | 46 | Pf LSA1 13 | 27.0403 | 15 |
| NLLIFHINGKIIKNS | 224 | Pf LSA1 15 | 27.0406 | 15 |
| QTNFKSLLRNLGVSE | 225 | Pf LSA1 94 | 27.0408 | 15 |
| AYKFVVPGAATPYAG | 57 | Pf SSP2 514 | 27.0412 | 15 |
| NVKYLVIVFLIFFDL | 50 | Pf SSP2 6 | 27.0415 | 15 |
| VKNVIGPFMKAVCVE | 79 | Pf.SSP2.223 | 27.0417 | 15 |
| WENVKNVIGPFMKAV | 82 | Pf SSP2 220 | 27.0418 | 15 |
| CSVVRRAFPHCLAFS | 226 | HBV.pol.534 | 1186.04 | 15 |
| FVQWFVGLSPTVWLS | 146 | HBV ENV 342 | 1186.06 | 15 |
| LAQFTSAICSVVRRA | 155 | HBV.pol.526 | 1186.10 | 15 |
| LVPFVQWFVGLSPTV | 161 | HBV.env.339 | 1186.15 | 15 |
| NLSWLSLDVSAAFYH | 227 | HBV POL 422 | 1186.18 | 15 |
| SFGVWIRTPPAYRPP | 165 | HBV.nuc.121 | 1186.25 | 15 |
| SPFLLAQFTSAICSV | 142 | HBV.pol.522 | 1186.26 | 15 |
| SSNLSWLSLDVSAAF | 228 | HBV POL 420 | 1186.27 | 15 |
| DKELTMSNVKNVSQT | 58 | Pf LSA1 81 | 1188.01 | 15 |
| AGLLGNVSTVLLGGV | 55 | Pf.EXP1.82 | 1188.13 | 15 |
| KSKYKLATSVLAGLL | 42 | Pf.EXP1.71 | 1188.16 | 15 |
| GLAYKFVVPGAATPY | 61 | Pf.SSP2.512 | 1188.32 | 15 |
| HNWVNHAVPLAMKLI | 64 | Pf.SSP2.62 | 1188.34 | 15 |
| IGPFMKAVCVEVEKT | 40 | Pf SSP2 227 | 1188.35 | 15 |
| KYKIAGGIAGGLALL | 229 | Pf.SSP2.494 | 1188.38 | 15 |
| RHNWVNHAVPLAMKL | 75 | Pf SSP2 61 | 1188.45 | 15 |
| IKQFINMWQEVGKAMY | 230 | HIV1.env.566 | F091.15 | 16 |
| LQSLTNLLSSNLSWL | 231 | HBV.pol.412 | F107.03 | 15 |
| PFLLAQFTSAICSVV | 140 | HBV.pol.523 | F107.04 | 15 |
| KYKLATSVLAGLLGN | 43 | Pf EXP1 173 | F107.09 | 15 |
| LAGLLGNVSTVLLGG | 69 | Pf EXP1 81 | F107.10 | 15 |
| RHPFKIGSSDPADNA | 76 | Pf EXP1 107 | F107.11 | 15 |
| ANQLVVILTDGIPDS | 56 | Pf SSP2 153 | F107.14 | 15 |
| KFVVPGAATPYAGEP | 66 | Pf SSP2 516 | F107.17 | 15 |
| VFNVVNSSIGLIMVL | 78 | Pf CSP 412 | F107.23 | 15 |
| VGPLTVNEKRRLKLI | 232 | HBV.pol.96 | 35.0093 | 15 |
| ESRLVVDFSQFSRGN | 233 | HBV.pol.387 | 35.0096 | 15 |
| LCQVFADATPTGWGL | 157 | HBV.pol.683 | 35.0100 | 15 |
| VVVVATDALMTGYTG | 234 | HCV.1437 | 35.0106 | 15 |
| TVDFSLDPTFTIETT | 235 | HCV.1466 | 35.0107 | 15 |
| AETFYVDGAANRETK | 236 | HIV.pol.619 | 35.0125 | 15 |
| EVNIVTDSQYALGII | 237 | HIV.pol.674 | 35.0127 | 15 |
| WAGIKQEFGIPYNPQ | 238 | HIV.pol.874 | 35.0131 | 15 |
| GAVVIQDNSDIKVVP | 239 | HIV.pol.989 | 35.0133 | 15 |
| YRKILRQRKIDRLID | 240 | HIV.vpu.31 | 35.0135 | 15 |
| PDSIQDSLKESRKLN | 241 | Pf.SSP2.165 | 35.0171 | 15 |
| KCNLYADSAWENVKN | 242 | Pf.SSP2.211 | 35.0172 | 15 |
| IGTVLVGPTPVNIIG | 115 | HIV.pol.152 | 1280.02 | 15 |
| KVYLAWVPAHKGIGG | 117 | HIV.pol.712 | 1280.03 | 15 |
| TKELQKQITKIQNFR | 126 | HIV.pol.952 | 1280.04 | 15 |
| AGFFLLTRILTIPQS | 145 | HBV.env.180 | 1280.06 | 15 |

TABLE VIII-continued

| | | | | |
|---|---|---|---|---|
| GFFLLTRILTIPQSL | 137 | HBV ENV 181 | 1280.08 | 15 |
| GTSFVYVPSALNPAD | 148 | HBV.pol.774 | 1280.09 | 15 |
| IIFLFILLLCLIFLL | 151 | HBV ENV 244 | 1280.12 | 15 |
| KFAVPNLQSLTNLLS | 154 | HBV POL 406 | 1280.13 | 15 |
| LHLYSHPIILGFRKI | 158 | HBV.pol.501 | 1280.15 | 15 |
| LLCLIFLLVLLDYQG | 159 | HBV ENV 251 | 1280.16 | 15 |
| VGLLGFAAPFTQCGY | 167 | HBV POL 637 | 1280.21 | 15 |
| FYFILVNLLIFHING | 60 | Pf LSA1 9 | 1280.22 | 15 |
| KSLLRNLGVSENIFL | 67 | Pf.LSA1.98 | 1280.23 | 15 |
| RGYYIPHQSSLPQDN | 74 | Pf.LSA1.1669 | 1280.25 | 15 |
| VYLLPRRGPRLGVRA | 243 | HCV Core 34 | 1283.02 | 15 |
| GHRMAWDMMMNWSPT | 244 | HCV E1 315 | 1283.10 | 15 |
| CGPVYCFTPSPVVVG | 245 | HCV.NS1/E2.506 | 1283.11 | 15 |
| VYCFTPSPVVVGTTD | 246 | HCV NS1/E2 509 | 1283.12 | 15 |
| GNWFGCTWMNSTGFT | 247 | HCV.NS1/E2.550 | 1283.13 | 15 |
| FTTLPALSTGLIHLH | 177 | HCV NS1/E2 684 | 1283.14 | 15 |
| SKGWRLLAPITAYAQ | 248 | HCV.NS3.1025 | 1283.16 | 15 |
| DLYLVTRHADVIPVR | 175 | HCV NS3 1134 | 1283.17 | 15 |
| AQGYKVLVLNPSVAA | 249 | HCV.NS3.1251 | 1283.20 | 15 |
| GYKVLVLNPSVAATL | 250 | HCV.NS3.1253 | 1283.21 | 15 |
| VLVLNPSVAATLGFG | 251 | HCV.NS3.1256 | 1283.22 | 15 |
| GARLVVLATATPPGS | 178 | HCV NS3 1345 | 1283.24 | 15 |
| DVVVVATDALMTGYT | 252 | HCV.NS3.1436 | 1283.26 | 15 |
| FTGLTHIDAHFLSQT | 253 | HCV.NS3.1567 | 1283.30 | 15 |
| YLVAYQATVCARAQA | 254 | HCV.NS3.1591 | 1283.31 | 15 |
| LEVVTSTWVLVGGVL | 255 | HCV NS4 1658 | 1283.33 | 15 |
| TWVLVGGVLAALAAY | 256 | HCV NS4 1664 | 1283.34 | 15 |
| AKHMWNFISGIQYLA | 257 | HCV.NS4.1767 | 1283.36 | 15 |
| IQYLAGLSTLPGNPA | 181 | HCV NS4 1777 | 1283.37 | 15 |
| MNRLIAFASRGNHVS | 258 | HCV.NS4.1921 | 1283.44 | 15 |
| SYTWTGALITPCAAE | 259 | HCV.NS5.2456 | 1283.50 | 15 |
| GSSYGFQYSPGQRVE | 260 | HCV.NS5.2641 | 1283.55 | 15 |
| LELITSCSSNVSVAH | 261 | HCV.NS5.2813 | 1283.57 | 15 |
| ASCLRKLGVPPLRVW | 262 | HCV.NS5.2939 | 1283.61 | 15 |
| VGNFTGLYSSTVPVF | 263 | HBV.pol.53 | 1298.02 | 15 |
| TNFLLSLGIHLNPNK | 264 | HBV.pol.568 | 1298.03 | 15 |
| KQCFRKLPVNRPIDW | 265 | HBV.pol.615 | 1298.04 | 15 |
| KQAFTFSPTYKAFLC | 266 | HBV.pol.661 | 1298.06 | 15 |
| AANWILRGTSFVYVP | 267 | HBV.pol.764 | 1298.07 | 15 |
| PDRVHFASPLHVAWR | 268 | HBV.pol.824 | 1298.08 | 15 |
| IRPVVSTQLLLNGSL | 269 | HIV1.env.333 | 1298.10 | 15 |
| RSELYKYKVVKIEPL | 270 | HIV1.env.637 | 1298.11 | 15 |
| DRFYKTLRAEQASQE | 271 | HIV1 GAG 333 | 1298.13 | 15 |
| KVILVAVHVASGYIE | 272 | HIV1.pol.813 | 1298.16 | 15 |
| LVNLLIFHINGKIIKNS | 273 | Pf.LSA1.13 | F125.02 | 17 |
| RHNWVNHAVPLAMKLI | 274 | Pf.SSP2.61 | F125.04 | 16 |

What is claimed is:

1. A method to screen peptides to distinguish candidate peptides for administration as an immunogen from peptides that are not candidate peptides for administration as an immunogen which method comprises (a) providing at least one peptide that bears a DR motif corresponding to a Class II HLA molecule;

(b) testing the peptide for binding affinity to a Class II HLA DR molecule, whereupon $IC_{50}$ binding affinity in nanomolar (nM) is determined;

(c) comparing the binding affinity of the peptide to an $IC_{50}$ affinity threshold of 1,000 nM; and (d) identifying as a candidate peptide for administration as an immunogen a peptide that binds said class II HLA DR molecule at an $IC_{50}$ of <1,000 nM, and identifying as a peptide not a candidate for administration as an immunogen, a peptide that binds said Class II HLA DR molecule at an $IC_{50}$ of >1,000 nM, thereby distinguishing candidate peptides for administration as immunogens from peptides not candidates for administration as immunogens.

2. A method to screen peptides to distinguish peptides which are T cell epitopes in the context of a DR molecule from peptides that are non T cell epitopes in the context of a DR molecule which method comprises (a) providing at least one peptide that bears a DR motif corresponding to a Class II HLA molecule;

(b) testing the peptide for binding affinity to a Class II HLA DR molecule, whereupon $IC_{50}$ binding affinity in nanomolar (nM) is determined;

(c) comparing the binding affinity of the peptide to an $IC_{50}$ affinity threshold of 1,000 nM; and (d) identifying as a T cell epitope that binds said Class II HLA DR molecule at an $IC_{50}$ of >1,000 nM, and identifying as not a T cell epitope a peptide that binds said Class II HLA DR molecule at an $IC_{50}$ of >1,000 nM, thereby distinguishing peptides that are T cell epitopes from peptides that are not T cell epitopes.

* * * * *

UNITED STATES PATENT AND TRADEMARK OFFICE
CERTIFICATE OF CORRECTION

PATENT NO. : 6,413,517 B1
DATED : July 2, 2002
INVENTOR(S) : Alessandro Sette, John Sidney and Scott Southwood It is certified that error appears in the above-identified patent and that said Letters Patent is hereby corrected as shown below:

Column 146,
Line 7, ">1,000 nM" should read -- <1,000 nM --.

Signed and Sealed this

Thirty-first Day of May, 2005

JON W. DUDAS
*Director of the United States Patent and Trademark Office*